US010147504B1

(12) United States Patent
Stettin et al.

(10) Patent No.: US 10,147,504 B1
(45) Date of Patent: Dec. 4, 2018

(54) METHODS AND SYSTEMS FOR DATABASE MANAGEMENT BASED ON CODE-MARKER DISCREPANCIES

(71) Applicant: Express Scripts Strategic Development, Inc., St. Louis, MO (US)

(72) Inventors: Glen D. Stettin, St. Louis, MO (US); Juliana Dierks, Berlin (DE)

(73) Assignee: Express Scripts Strategic Development, Inc., St. Louis, MO (US)

(*) Notice: Subject to any disclaimer, the term of this patent is extended or adjusted under 35 U.S.C. 154(b) by 0 days.

(21) Appl. No.: 14/060,513

(22) Filed: Oct. 22, 2013

Related U.S. Application Data

(60) Provisional application No. 61/717,075, filed on Oct. 22, 2012.

(51) Int. Cl.
*G16H 50/30* (2018.01)

(52) U.S. Cl.
CPC .................. *G16H 50/30* (2018.01)

(58) Field of Classification Search
CPC .. G06F 19/322; G06F 19/325; G06F 19/3431; G06F 19/345; G06Q 50/24; G16H 50/30
USPC ............................................................. 705/2
See application file for complete search history.

(56) References Cited

U.S. PATENT DOCUMENTS

| | | | | |
|---|---|---|---|---|
| 5,970,463 | A * | 10/1999 | Cave | G06F 19/322 705/2 |
| 7,698,155 | B1 | 4/2010 | Prasad et al. | |
| 7,716,067 | B2 | 5/2010 | Surpin et al. | |
| 7,725,330 | B2 * | 5/2010 | Rao | G06F 19/328 705/2 |
| 8,015,136 | B1 * | 9/2011 | Baker | G06F 19/322 706/45 |
| 2004/0172297 | A1 * | 9/2004 | Rao | G06F 19/328 705/2 |
| 2006/0036536 | A1 * | 2/2006 | Williams et al. | 705/38 |
| 2007/0214013 | A1 * | 9/2007 | Silverman | G06F 19/3431 705/2 |
| 2013/0144641 | A1 | 6/2013 | Bessette | |

* cited by examiner

*Primary Examiner* — Hiep V Nguyen
(74) *Attorney, Agent, or Firm* — Husch Blackwell LLP

(57) ABSTRACT

Methods and systems for risk assessment and adjustment are described. In one embodiment, a patient-level risk score associated with a patient is calculated. A plan-level average risk score associated with a benefit plan is calculated. The patient is a member of the benefit plan. A missing diagnosis code associated with the patient is identified based on medical claims history of the patient, historical prescription drug claims of the patient, and a drug marker. A revised patient-score associated with the patient is calculated based on identification of the missing diagnosis code. Additional methods and systems are disclosed.

16 Claims, 15 Drawing Sheets

| Definition Metric | Asthma / COPD | | Hemophilia |
|---|---|---|---|
| (1) ICD-9 Diagnosis Codes | 493.0 Extrinsic asthma<br>493.1 Intrinsic asthma<br>493.2 Chronic obstructive asthma<br>493.8 Other forms of asthma<br>493.9 Asthma, unspecified | 491 Chronic bronchitis<br>492 Emphysema<br>493.2 Chronic obstructive asthma<br>496 Chronic airway obstruction | 286.0 Congenital factor VIII disorder<br>286.1 Congenital factor IX disorder<br>286.2 Congenital factor XI deficiency<br>286.3 Congenital deficiency of other clotting factors |
| (2) Rx History | - Asthma meds | - Asthma meds | - Specific GPI group<br>- Desmopressin (30-20-10-10)<br>- Rapid interventions<br>- Smaller qty's with more frequency |
| (3) Socio-Demographics | - Younger patients<br>- Prevalence difference among ethnic groups | - Older patients | - Typically male, young boys<br>- Von Willebrand's disease if female<br>- Majority will be diagnosed as hemophilia type A, factor VII (80% of ptnts)<br>- 20% will be type B, factor IX |

METAL TIER VIEW

| | RISK SCORE | | CLIENT VS PRIOR YR. | | CLIENT VS BENCHMARK | |
|---|---|---|---|---|---|---|
| | CLIENT PRIOR YR. | BENCHMARK TODAY | CLIENT TODAY | DIFFERENCE FAV/(UNFAV) | # VS PRIOR YR. | DIFFERENCE FAV/(UNFAV) | % VS BENCHMARK |
| TOTAL | 1.0672 | 1.0275 | 1.1587 | 0.0915 △ | +8.6% | 0.1312 △ | +12.8% |
| PLATINUM | 1.1031 | 1.1708 | 1.1093 | 0.0062 △ | +0.6% | (0.0615) ▽ | -5.3% |
| GOLD | 1.3105 | 1.2879 | 1.3221 | 0.0116 △ | +0.9% | 0.0341 △ | +2.7% |
| SILVER | 1.6123 | 1.5901 | 1.6413 | 0.0290 △ | +1.8% | 0.0512 △ | +3.2% |
| BRONZE | 1.6901 | 1.6328 | 1.7217 | 0.0316 △ | +1.9% | 0.0889 △ | +5.4% |
| CATASTROPHIC | 1.7150 | 1.7097 | 1.7282 | 0.0132 △ | +0.8% | 0.0184 △ | +1.1% |

VIEW DETAILS

STATE VIEW

| | RISK SCORE | | | CLIENT VS PRIOR YR. | | CLIENT VS BENCHMARK | |
|---|---|---|---|---|---|---|---|
| | CLIENT PRIOR YR. | BENCHMARK TODAY | CLIENT TODAY | DIFFERENCE FAV/(UNFAV) | # VS PRIOR YR. | DIFFERENCE FAV/(UNFAV) | % VS BENCHMARK |
| TOTAL | 1.0672 | 1.0275 | 1.1587 | 0.0915 △ | +8.6% | 0.1312 △ | +12.8% |
| OHIO | 1.1031 | 1.0623 | 1.1654 | 0.0623 △ | +5.6% | 0.1031 △ | +9.7% |
| S. CAROLINA | 1.3105 | 1.3312 | 1.3218 | 0.0113 △ | +0.9% | (0.0094) ▽ | -0.7% |
| GEORGIA | 1.6123 | 1.5927 | 1.6302 | 0.0179 △ | +1.1% | 0.0375 △ | +2.4% |

VIEW DETAILS

HHS CONDITION VIEW

| | RISK SCORE | | | CLIENT VS PRIOR YR. | | CLIENT VS BENCHMARK | |
|---|---|---|---|---|---|---|---|
| | CLIENT PRIOR YR. | BENCHMARK TODAY | CLIENT TODAY | DIFFERENCE FAV/(UNFAV) | # VS PRIOR YR. | DIFFERENCE FAV/(UNFAV) | % VS BENCHMARK |
| TOTAL | 1.0672 | 1.0275 | 1.1587 | 0.0915 △ | +8.6% | 0.1312 △ | +12.8% |
| ASTHMA | 1.1031 | 1.1381 | 1.1166 | 0.0135 △ | +1.2% | (0.0215) ▽ | -1.9% |
| CHF | 1.3105 | 1.3533 | 1.3218 | 0.0113 △ | +0.9% | (0.0316) ▽ | -2.3% |
| CYSTIC FIBROSIS | 1.6123 | 1.6163 | 1.6207 | 0.0084 △ | +0.5% | 0.0045 △ | +0.3% |
| DIABETES | 1.6901 | 1.5380 | 1.7392 | 0.0491 △ | +2.9% | 0.2013 △ | +13.1% |
| MS | 1.4263 | 1.4560 | 1.4345 | 0.0091 △ | +0.6% | (0.0215) ▽ | -1.5% |

VIEW DETAILS

METHODS AND SYSTEMS FOR DATABASE MANAGEMENT BASED ON CODE-MARKER DISCREPANCIES

CROSS-REFERENCE TO A RELATED APPLICATION

This application claims the benefit of U.S. provisional patent application 61/717,075 filed on 22 Oct. 2012, entitled "Method and Systems for Risk Assessment and Adjustment," the entire disclosure of which is incorporated herein by reference.

FIELD

The field relates to health benefit plans, and more particularly to assessing and adjusting to risk associated with patient treatment.

BACKGROUND

Pharmacy benefit managers, as part of its services, typically provide prescription drug programs for clients that may, for example, sponsor drug benefit programs for members. As part of the providing the prescription drug programs for clients, pharmacy benefit managers may adjudicate claims from pharmacies for prescriptions obtained by members at the pharmacy. The PBM may also reimburse pharmacies for prescription obtained by members at the pharmacies. The PBM may also bill clients for the cost of prescriptions adjudicated by the pharmacy benefit manager.

BRIEF DESCRIPTION OF THE DRAWINGS

FIGS. 10-16 are example diagrams, according to example embodiments; and

DETAILED DESCRIPTION

Figure 1:
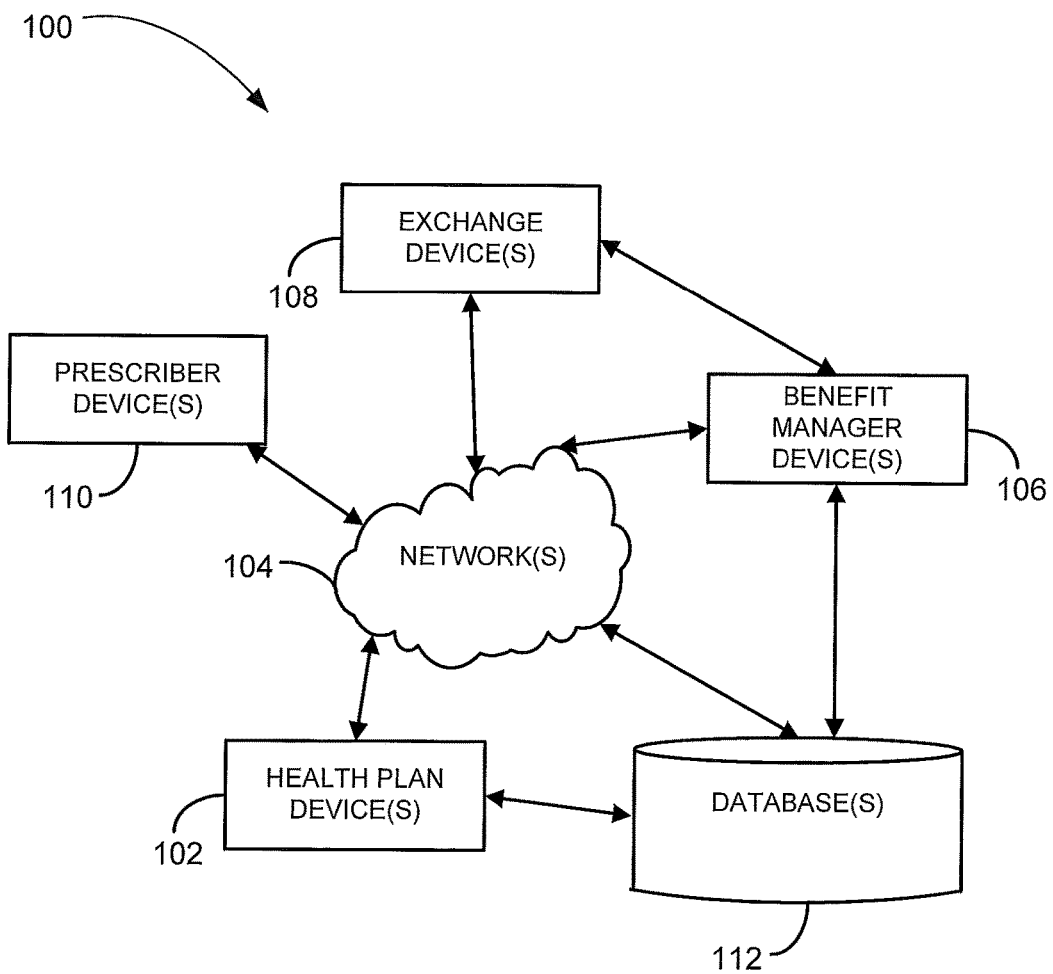
FIG. 1 is a block diagram of an example system, according to an example embodiment.

Example methods and systems for performing risk assessment and adjustment are described. In the following description, for purposes of explanation, numerous specific details are set forth in order to provide a thorough understanding of example embodiments. It will be evident, however, to one of ordinary skill in the art that embodiments of the invention may be practiced without these specific details.

Within implementation of government healthcare exchanges, health plans will be assessing their population's risk. The risk may not be based on typical surveys performed by health plans, but rather based on rules that have not yet been introduced and/or implemented. These rules may be driven off of diagnosis codes. The health plans may determine what percentage of their population has (or will have) diabetes, renal failure, or the like and which have no diagnosis are considered healthy.

The methods and systems relate to assessment of a population of patients or members of a health plan that are receiving health benefit services under a governmental established healthcare exchange. The government healthcare exchanges may have or use a methodology to determine which diagnoses are significant and the corresponding weight attached to each diagnosis. For example, a renal failure patient may count as 3 persons/patients, a healthy person may counts as 0.8 persons/patients, and the like.

The health plans participating in the exchange may determine an aggregated average for their entire patient portfolio for those patients in the exchange, per every patient, or the like. Thus, if one health plan underwrites renal failure patients and has an average factor of 3 and another plan has healthy patients with a 0.8 factor, the healthy plan may be required to compensate the other plan for their added risk. By capturing missing diagnosis codes, the health plan may be compensated appropriately based on a more accurate patient population. The diagnosis codes may be missing due to error (e.g., in code entry), a patient being diagnosed with a condition but having not been associated with a diagnosis code, or otherwise.

In some embodiments, medical cost will be a factor in addition to disease state. For example, not all diabetic patients are the same. The health plan may have some patients that will cost the health plan more and other patients that cost the health plan less.

In some embodiments, the methods and systems may be used to assist health plans with their risk adjustment methodology. In some embodiments, the methods and systems may be used to identify potential coding gaps and send associated information to health plans for resolution. In some embodiments, the methods and systems may be used to identify or further identify certain types of patients or members that are receiving health care.

In some embodiments, the methods and systems may be used to identify a missing diagnosis code faster than would not otherwise be identified or readily identified. Such identification may provide for earlier payment, may provide for a payment that would otherwise be time barred, may provide for enhanced payment or reimbursement, or otherwise.

In some embodiments, the current regulations rely on the diagnoses reported on certain hospital inpatient facility, hospital outpatient, and physician provider claims. Diagnoses are acceptable from a qualified provider. In accordance with regulations, the methods and systems may incorporate multiple provider types and claims types as sources of diagnoses information.

The methods and systems use drug markers as early identifiers of risk. To the extent that a patient has a drug marker, they are assumed to have a corresponding diagnosis. The methods and systems focus on identification and intervention on gaps. In embodiments in which the persistency of chronic conditions and complications of diseases are part of the risk calculation such as part of the U.S. Department of Health and Human Services (HHS) guidelines, they may be used in the risk score calculation and gap identification, along with other HHS-specified conditions. The methods and systems may thus be used to identify undocumented or inappropriately documented diagnoses and close those gaps.

In some embodiments, the methods and systems may prompt action by patients and physicians, as well as clients, to drive better decisions that improve clinical and financial outcomes. In some embodiments, patient interventions may include targeted outreach to drive patients to their physician. In some embodiments, physician interventions may include targeted outreach to confirm and re-submit an existing medical and/or prescription drug claim.

In some embodiments, the methods and systems identify and prioritize gaps for intervention. Identification of these gaps then generates alerts. The alerts may be displayed on a website to patients and physicians, via a mobile app, or otherwise. The alert may provide clinical rationale and create the urgency for the patient or physician to take action.

In some embodiments, the methods and systems may be usable to health plans so that the health plans offer different patients different prices that still fall within the actuarial value. In some embodiments, medical cost may be a factor in addition to disease state with respect to a single entity or multiple entities that deploy and/or utilize the assessment and adjustment subsystem 202.

FIG. 1 is a block diagram of an example system 100, according to an example embodiment. The system 100 is an example environment in which risk assessment and adjustment may be performed. The system 100 includes a health plan device 102 in communication with a benefit manager device 106, an exchange device 108, and/or a prescriber device 110 over a network 104.

The health plan device 102 is a device operated by an entity at least partially responsible for creation and/or management of a health benefit. In some embodiments, the health plan device 102 may perform a population risk assessment on its patients/members. The population risk assessment may be performed on the basis of diagnosis codes, or otherwise. The population risk assessment may then be provided to the exchange device 108. In some embodiments, the operator of the health plan device 102 is a client of a benefit manager that operates the benefit manager device 106.

The network 104 by which the mobile electronic device 102 communicates with the benefit manager device 106, the exchange device 108, and/or the prescriber device 110 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The benefit manager device 106 is a device operated by an entity at least partially responsible for creation and/or management of the pharmacy benefit. While the benefit manager operating the benefit manager device 106 is typically a pharmacy benefit manager (PBM), other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. The prescription drug may otherwise be received through a different delivery channel such as a prescription drug kiosk station.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member and/or a prescription/health/medical benefit plan may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a drug utilization review (DUR) on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network.

The exchange device 108 is a device used by an exchange that is offering benefits provided by a health plan. In some embodiments, the exchange is a public exchange. In some embodiments, the exchange is a private exchange. The exchange device 108 may receive population risk assessments from multiple health plan devices 102 associated with different health plans to compute which health plans exchange funds to account for different respective patient populations.

In some embodiments, the benefit manager device 106 may assist the health plan device 102 in determining its population risk assessment by capturing diagnosis codes. In some embodiments, the benefit manager device 106 may provide the health plan device 102 with a list of patients that are likely missing diagnosis codes. In some embodiments, the benefit manager device 106 may identify the missing diagnosis codes associated with patients. The identification may include telemedicine calls with the patients or other outreach (e.g., at the physician's office) in an attempt to have the diagnosis codes entered into the patient's medical record. The diagnosis codes may be entered in the patient's medical record through medication of an electronic medical record, alteration of or addition of one or more prescription drug claims, alteration or addition of one or more medical claims, or otherwise.

The prescriber device 112 may be operated by, or on behalf of, a medical care professional or prescriber that may prescribe a course of treatment that may include a prescribed drug for a patient. In general, the medical care professional operating a prescriber device 112 is a person that is capable of writing a prescription or script for a medication. Examples of prescribers include doctors, nurse practitioners, and dentists. In some embodiments, the prescribers may be part of a physician network. For example, the physician network may be able to obtain legally valid scripts in one or more of the states or other geographic regions. The medical care professional may use the prescriber device 112 to review information received about a patient and approve the patient to have or otherwise receive an electronic script for a medication (e.g., a prescription drug). In general, the electronic script is for a particular member. However, in some embodiments the electronic script may be for a group of people (e.g., a member and the member's family). In some embodiments, the prescriber may provided the patient with a paper script instead of, or in addition to, the electronic script. The paper script may be provided with or without using the prescriber device 112. In some embodiments, the prescription is written electronically, in paper, or otherwise for a patient who is not a member of a prescription drug benefit.

In some embodiments, the prescriber device 112 may be utilized by the medical care professional to transmit a prescription associated with a patient (who may be a member of the drug benefit program) to a pharmacy (e.g., via the pharmacy device 108) and/or to the benefit manager device 106. The pharmacy, to which the prescription may be transmitted, may be a retail pharmacy location, a mail order pharmacy, or another type of drug dispensing facility.

The health plan device 102 may be in a client-server relationship with the benefit manager device 106 and/or the exchange device 108, a peer-to-peer relationship with the benefit manager device 106 and/or the exchange device 108, or in a different type of relationship with the benefit manager device 106 and/or the exchange device 108.

The health plan device 102 and/or the benefit manager device 106 may be in communication directly (e.g., through local storage) and/or through the network 104 (e.g., in a cloud configuration or software as a service) with a database 112. The health plan device 102 and the benefit manager device 106 may share a database, have separate databases, or share one or more databases and also have separate databases.

The database 112 may be deployed on the health plan device 102 and the benefit manager device 106, on more than one of the devices 102, 106, partially on more than one of the devices 102, 106, or may otherwise be deployed. The deployment may occur on local storage, remote storage, removable storage, and/or a different type of storage associated with the devices 102, 106. Additionally, while a single database is depicted, multiple databases may be implemented. In the case of multiple databases, the different databases may be deployed on different systems, including the devices 102, 106, /or a third-party device or network.

The database 112 may store member data, client data, prescriber data, claims data, clinical data, and the like. The database 112 may also store different types of data.

The database 112 may include member data that includes information regarding the members associated with the benefit manager. Examples of the member data 112 include name, address, telephone number, e-mail address, prescription drug history, and the like. The member data 112 may include a client identifier that identifies the client (e.g., a health plan) associated with the member and/or a member identifier that identifies the member to the client.

The database 112 may include client data that includes information regarding the clients of the benefit manager. Examples of the client data include company name, company address, contact name, contact telephone number, contact e-mail address, and the like.

The database 112 may include prescriber data that includes information regarding prescribers. The prescriber data may include, by way of example, location data regarding the location of the prescribers, information data regarding the prescriber hours and/or telephone number, prescriber network association data defining the prescriber network associations of which the prescribers are associated, and the like. The prescribers may be at a physician's office, a hospital, a location associated with a PBM, or the like.

The database 112 may include claims data that provides information regarding pharmacy claims adjudicated by the PBM under a drug benefit program provided by the PBM for one, or more than one, clients. In general, the claims data may include client data (e.g., including an identification of the client that sponsors the drug benefit program under which the claim is made, company name, company address, contact name, contact telephone number, contact email address, and the like), an identification of the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. The claims data may also include claims adjudicated for health care related services other than prescriptions filled under a drug benefit program. Examples of other healthcare related services may include medical services (such as treatment, screening services, laboratory services), dental related services, and vision care related services. Additional information may be included in the various claims of the claims data.

Clinical data may be included as part of and/or separate from the claims data. The clinical data includes clinical records regarding member diagnosis and/or therapy. The clinical records may be obtained from hospitals, medical insurance companies, drug trials, medical laboratories and/or the member via online questionnaires, for example. In some embodiments, the database 112 may include electronic medical records (EMR).

In some embodiments, the medical claims data received by the benefit manager device 106 is matched against the eligibility files received by or available to the benefit manager. The medical claims may then be linked with prescriptions claims to provide a more complete picture of the patient's history.

Various portions of the data may be validated. For example, medical data validation may vary based on the source and quality of the data provided to the benefit manager device 106. Some of the validations that may be performed on medical data include validation of diagnosis and procedure codes, distribution of place of service codes, distribution of claims types (e.g., inpatient, outpatient, office visit, etc), validation on gender appropriateness of diagnosis or procedure, determination of appropriateness of claim volumes for a size of a client, and the like.

While the system 100 in FIG. 1 is shown to include single devices 102, 106, 108, 110, multiple devices may be used. The devices 102, 106, 108, 110 may be the same type of device or may be different device types. When multiple devices are present, the multiple devices may be of the same device type or may be a different device type. Moreover, system 100 shows a single network 104; however, multiple networks can be used. The multiple networks may communicate in series with each other to link the devices 102, 106, 108, 110 or in parallel to link the devices 102, 106, 108, 110.

In some embodiments, at least some of the functionality of the benefit manager device 106 and/or the exchange device 108 may be included in the health plan device 102.

Figure 2:
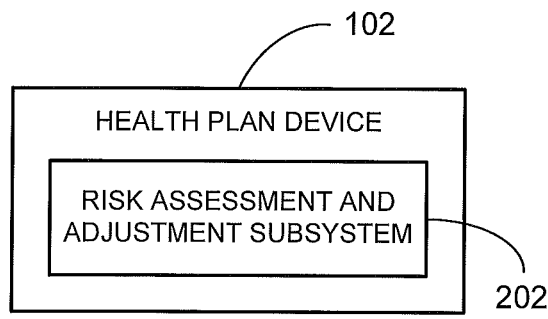
FIG. 2 is a block diagram of an example health plan device that may be deployed within the system of FIG. 1, according to an example embodiment.

FIG. 2 illustrates the health plan device 102, according to an example embodiment. The health plan device 102 may be deployed in the system 100, or may otherwise be used. The health plan device 102 may include a risk assessment and adjustment subsystem 202 to determine risk assessment and adjustment.

The risk assessment and adjustment subsystem 202 may provide for one, or more than one, of patient and/or plan risk score calculation, patient and/or physician gap identification, patient and/or physician intervention for gap closure, and risk and/or intervention reporting.

In some embodiments, the risk assessment and adjustment subsystem 202 follows some or all of the HHS requirements to calculate the patient level risk score and plan level average risk score. In some embodiments, the patient score is the combination (e.g., sum) of patient diagnostic risk score and demographic risk score. In some embodiments, the plan average risk score is a weighted risk score at the plan level.

In some embodiments, the risk assessment and adjustment subsystem 202 identifies on the list of conditions targeted by HHS for risk adjustment those conditions that support drug code-to-condition mapping. For patients on therapy for these conditions, their medical claims history is compared to historical claims for drug markers to identify potential gaps. The potential gaps may include patient gaps and/or physician gaps. The patient gaps may include patients who do not have any medical claims but are identified as having one of the respective drug markers. The physician gaps may include physicians treating one or more patients who have a drug marker but do not have the anticipated ICD9/ICD10 diagnosis codes on a medical claim. Based on this comparison, the risk assessment and adjustment subsystem 202 may report on patient-level details such as patient risk score, number of gaps, and conditions associated with a particular gap, and the like. The risk assessment and adjustment subsystem 202 and/or personnel at an organization (e.g., nurses operating under the direction of the benefit manager) may intervene at patient and physician level to close these gaps. In some embodiments, the closure of these gaps leads to an increase in patient-level diagnostic risk score. In some embodiments, the closure of these gaps leads to a more accurate total patient risk score and the plan average risk score.

The risk assessment and adjustment subsystem 202 may generate initial, interim, and/or year-end risk scores at patient and plan levels for client review. Other ad hoc reports may also be generated.

In some embodiments, the risk assessment and adjustment subsystem 202 combines risk intelligence analytics with risk interventions to identify and drive meaningful engagement of the targeted patients and physicians. The risk assessment and adjustment subsystem 202 may analyze integrated data, including medical claims data, real-time pharmacy claims data, potential retrospective pharmacy claims data and other available data sources for early identification of risk resulting in detection and prioritization of potential risk gaps. The assessment and adjustment subsystem 202 may leverage behavioral sciences to apply messaging principles that drive patients and/or physicians to take action. The assessment and adjustment subsystem 202 may, directly or on behalf of the benefit manager or another entity, utilize written and verbal communications and clinical expertise to engage with patients and/or physicians in the management of their chronic condition(s) to motivate patient and physician action to close gaps in care.

In some embodiments, the assessment and adjustment subsystem 202 may collect, integrate and analyze patient and physician data to provide actionable insights for addressing gaps in care that may include clinical and financial outcomes. The data used may include medical data, pharmacy data (e.g., real-time pharmacy data and/or historical pharmacy data), self collected data, and the like. The assessment and adjustment subsystem 202 may calculate individual risk scores, economic projection, and actuarial risks. The assessment and adjustment subsystem 202 may provide payments/charges validation support. The assessment and adjustment subsystem 202 may output clinical and economic reporting and identification of data integrity gaps, as well as benchmarking data, targeted lists, activity, and outcomes.

Figure 3:
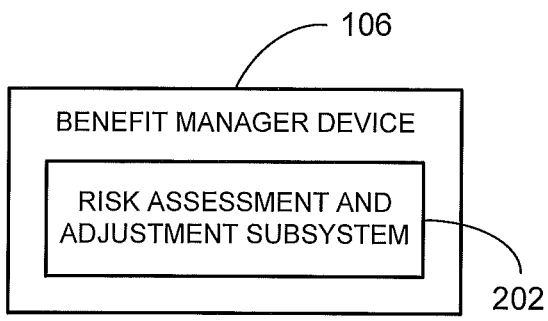
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used. The health plan device 102 may include the risk assessment and adjustment subsystem 202 to determine risk assessment and adjustment.

Figure 4:
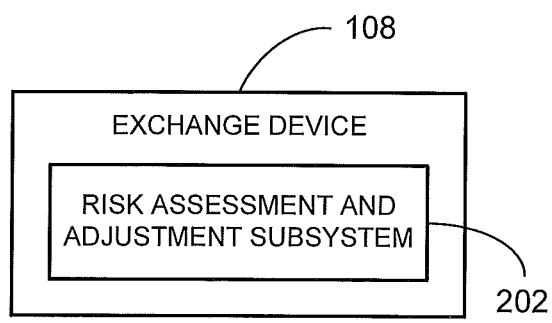
FIG. 4 is a block diagram of an example exchange device that may be deployed within the system of FIG. 1, according to an example embodiment.

FIG. 4 illustrates the exchange device 108, according to an example embodiment. The exchange device 108 may be deployed in the system 100, or may otherwise be used. The exchange device 108 may include the risk assessment and adjustment subsystem 202 to determine risk assessment and adjustment.

Figure 5:
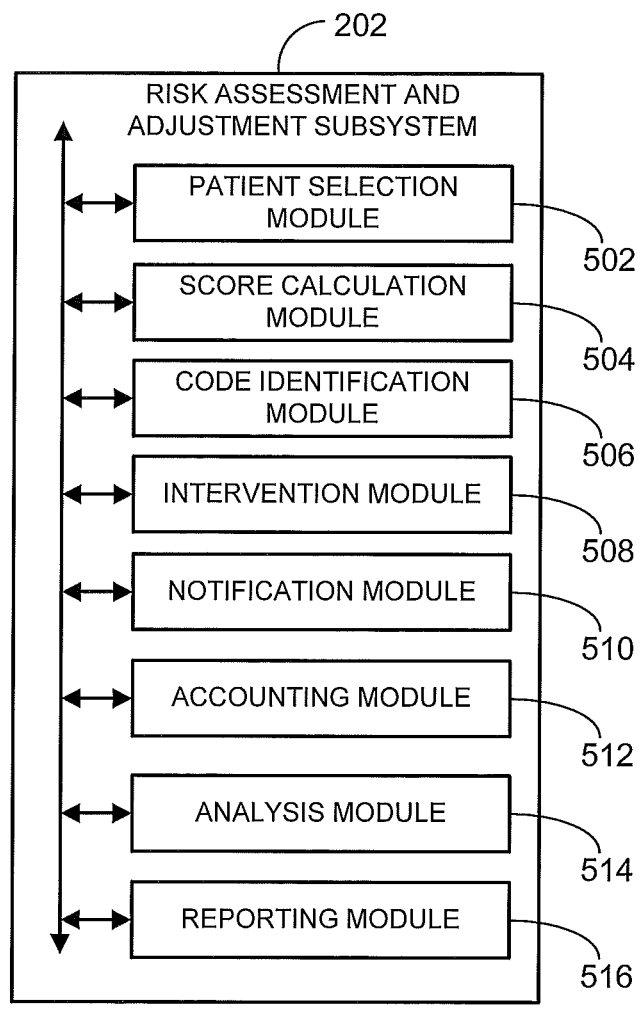
FIG. 5 is a block diagram of an example risk assessment and adjustment subsystem that may be deployed within the health plan device of FIG. 2, the benefit manager device of FIG. 3, or the exchange device of FIG. 4, according to an example embodiment.

FIG. 5 illustrates an example risk assessment and adjustment subsystem 202 that may be deployed in the health plan device 102, the benefit manager device 106, the exchange device 108, or otherwise deployed in another system. One or more modules are communicatively coupled and included in the risk assessment and adjustment subsystem 202 to perform risk assessment and adjustment. The risk assessment and adjustment subsystem 202 that may be included are a patient selection module 502, a score calculation module 504, a code identification module 506, an intervention module 508, a notification module 510, an accounting module 512, an analysis module 514, and/or a reporting module 516. Other modules may also be included.

In some embodiments, the modules of the risk assessment and adjustment subsystem 202 may be distributed so that some of the modules are deployed in the benefit manager device 106 and some of the modules are deployed in the health plan device 102 and/or the exchange device 108. In one embodiment, the modules are deployed in memory and executed by a processor coupled to the memory. The functionality contained within the modules 502-516 may be combined into a lesser number of modules, further divided among a greater number of modules, or redistributed among existing modules. Other configurations including the functionality of the modules 502-516 may be used.

In some embodiments, risk assessment and adjustment is performed by the risk assessment and adjustment subsystem 202 on a single patient. In other embodiments, risk assessment and adjustment is performed by the risk assessment and adjustment subsystem 202 on multiple patients. The determination of whether to perform the risk assessment and adjustment may be made by the health plan, the benefit manager, an operator of the exchange, or otherwise.

By way of example, the patient selection module 502 may pull eligible patients of a health plan for one, or more than one, client (e.g., of a health plan). The patient selection module 502 may then select a single patient, or multiple patients (e.g., all or a subset of patients of a client or a health plan). An example criterion that may be used to select a patient is that the patient is on a therapy for a condition that supports drug code-to-condition mapping.

In some embodiments, the patient selection module 502 identifies eligible patients during an analysis period for a client (e.g., a single client or multiple clients). Certain patients may be excluded by the patient selection module 502. For example, patients having age or gender missing and/or patients having both completed pregnancy records and newborn records may be excluded. In some embodiments, the exclusions may be made in accordance with rules or guidance provided by HHS.

In some embodiments, the patient selection module 502 reviews a patient population for a drug marker and then seeks associated medical claims that would then confirm or identify a gap.

After one, or more than one, patient is identified, the score calculation module 504 calculates a patient-level risk score for the selected patients. The score calculation module 504 may also calculate a plan-level average risk score associated with a benefit plan of which the patients are associated. In some embodiments, the plan-level average risk score is a weighted risk score at a plan level. The patient-level risk score and/or the plan-level average risk score may be calculated in one or a number of different ways. In some embodiments, calculation of the patient-level risk score and/or the plan-level average risk score may be driven by HHS requirements and may be adjusted or implemented accordingly.

The score calculation module 504 may then extract medical claims during an analysis time period for the selected patients on professional claims based on a professional source of diagnosis, inpatient facility claims based on an inpatient facility source of diagnosis, and/or outpatient claims based on an outpatient facility source of diagnosis. Other types of medical claims may also be extracted. In some embodiments, the extraction may be made in accordance with HHS requirements.

Based on the extracted medical claims, the score calculation module 504 may assign condition categories to each patient based on drug code-to-condition mapping (e.g., HHS ICD9 to condition mapping). In addition, hierarchical condition categories, condition groups, and/or severe illness interaction group values may be generated (e.g., per HHS specification). These risk factors, along with demographic factors, may be used by the score calculation module 504 to generate a risk score for each patient. The patient may be assigned a demographic value by the score calculation module 504 based on age and gender. The demographic risk score may then be calculated by the score calculation module 504 based on assignment of the demographic value.

In some embodiments, the score calculation module 504 calculates hierarchical condition categories (HCC) values. HHS may provide a hierarchy amongst condition categories and the hierarchy may be defined by the HCC values. By way of example, if a patient is assigned to all three HCCs for a condition based on the diagnosis in medical claims 19 (Diabetes with acute complications), 20 (Diabetes with chronic complications), 21 (Diabetes without complications) per the HHS hierarchy, the patient would be assigned an HCC of 19.

HHS may provide a detailed mapping of condition categories and how they align with the various hierarchies. The methods and systems may follow the same mapping by first assigning patients to condition categories and further assigning the hierarchy based on FIRS mapping. For example, if a patient has all three condition categories for Diabetes—19 (Diabetes with acute complication), 20 (Diabetes with chronic complication), and 21 (Diabetes without complication), the methods and systems may assign the highest hierarchy of 19 (Diabetes with acute complication). The hierarchy may be used to assign the diagnostic risk score through use of the HHS mapping.

The score calculation module 504 may generate HCC group values and severity interaction values per HHS specification.

In some embodiments, the risk score is calculated by the score calculation module 504 at each tier of a health plan based on the tier in which a patient is enrolled. Based on the demographic values, the demographic score is calculated by the score calculation module 504. The diagnostic score may take into account the weights provided to each HCC value and the severity interaction values. In some embodiments, HHS may provide weights based on the demographic values, HCC values, and severity values and this mapping may be used to assign the diagnostic and demographic score at the patient level.

In some embodiments, the score calculation module 504 calculates the plan average risk score with the weights being the billable month for each patient.

The determination of risk adjustment payments and transfers may be based not only on a health plan's risk score but also on other plan attributes normalized against the market (e.g., across a state, a city, a region, nationwide, or otherwise). In some embodiments, the score calculation module 504 adjusts for normalization factors in the calculation of premium transfer per HHS proposed ruling:

$$T_i = \left[ \frac{PLRS_i \times IDF_i \times GCF_i}{\sum_i (s_i \times PLRS_i \times IDF_i \times GCF_i)} - \frac{AV_i \times ARF_i \times IDF_i \times GCF_i}{\sum_i (s_i \times AV_i \times ARF_i \times IDF_i \times GCF_i)} \right] \times P_s$$

Where,
Ps=State average premium,
PLRSi=plan i's plan liability risk score,
AVi=plan i's metal level AV (Actuarial Value), ARFi=allowable rating factor
IDFi=plan i's induced demand factor,
GCFi=plan i's geographic cost factor,
si=plan i's share of State enrollment; and the denominator is summed across all plans in the risk pool in the market in a state.

In some embodiments, the score calculation module 504 calculates the patient-level risk score by accessing medical claims included in the medical claims history of the patient, calculating a demographic risk score, calculating a patient diagnostic risk score, and combining the demographic risk score and the patient diagnostic risk score to calculate the patient-level risk score. The combination may be made by summing the demographic risk score and the patient diagnostic risk score to calculate the patient-level risk score or otherwise. The medical claims may be accessed (e.g., from the database 112) by the score calculation module 504 based on a professional source of diagnosis, an inpatient facility source of diagnosis, and an outpatient facility source of diagnosis.

In some embodiments, a Chronic Disease Score (CDS) may be used by the score calculation module 504 as a risk adjuster for research studies. The CDS may be based off of a combination of drug rules and demographic data (e.g., age, gender, and the like) and, in some embodiments, is predictive of overall pharmacy cost. In addition to giving each patient an overall score, the CDS may be used as a way to identify people with certain conditions when only pharmacy claims data is available. An iteration of the CDS includes 52 different conditions each with a different weight based on the drug cost for each condition.

The score calculation module 504 may capture co-morbidities to determine whether or not to perform aggregate scoring across a patient population of a health plan. In an example embodiment, all diagnosis is reviewed. In an example embodiment, only the most prominent diagnosis is reviewed. For example, a patient could have unstable angina pectoris and Myocardial Infarction (MI). The patient could be scored on both conditions, or the MI condition may be taken since unstable angina pectoris could lead to MI. In some embodiments, a hierarchy within conditions established by the state or otherwise may be used.

In some embodiments, the code identification module 506 identifies a missing diagnosis code associated with the patient based on medical claims history of the patient, historical prescription drug claims of the patient, and a drug marker. In some embodiments, the code identification module 506 identifies the patient as not having an anticipated diagnosis code based on medical claims history of the patient, historical prescription drug claims of the patient, and a drug marker. The diagnosis code may be an ICD-9 diagnosis code, an ICD-10 diagnosis code, or other type of diagnosis code.

In some embodiments, the drug marker is a prescription drug or supply in the prescription history of the patient that is usable to identify the patient as having a medical condition. For example, the supply may be test strips contained within a medical claim. In some embodiments, the drug marker is a prescription drug or supply that generally relates to the patient having a medical condition. In some embodiments, the drug marker includes a prescription drug or supply in the prescription history of the patient that has been identified as being usually, or always, associated with a particular medical condition. Thus, when a drug marker is identified in the prescription history, the expectation is that the patient that features the drug marker has a certain medical condition regardless. In certain instances, the patient may have a drug marker indicating that he or she has a medical condition but the medical history of the patient may not include a diagnosis code associated with the medical condition, or may have an unanticipated diagnosis code.

In some embodiments, the drug markers have been created by mapping the prescription drugs taken by a patient population with knowledge of the medical conditions possessed by the patient population to identify which prescription drugs are or are likely to be identifiers, or markers, for certain medical conditions. The mapping may be created by rules based and/or predictive modeling software, by clinical expertise, and/or by other methods.

In some embodiments, identification of the missing diagnosis code by the code identification module 506 includes comparing the medical claims history of the patient to the historical prescription drug claims of the patient for the drug marker, and determining that the patient does not have a medical claim associated with the drug marker based on comparison of the medical claims history to the historical prescription drug claims and/or a drug code-to-condition mapping. The code identification module 506 may flag the patient as having the missing diagnosis code, associate the patient with the missing diagnosis code, or otherwise. In some embodiments, the notification module 510 transmits a patient flag notification based on flagging the patient as having the missing diagnosis code and receives a patient flag response in response to transmission of the patient flag notification. The patient flag notification may be received by the health plan device 102, the prescriber device 110, or otherwise. The receiver of the patient flag notification may make interventions or otherwise take actions to close a potential gap. The patient flag response may then identify the actions taken by the receiver.

In some embodiments, identification of the patient as not having an anticipated diagnosis code includes comparing the medical claims history of the patient to the historical prescription drug claims of the patient for the drug marker, determining that the patient has the drug marker but does not have the anticipated diagnosis code of a medical claim associated with the drug marker, and flagging the patient as not having the anticipated diagnosis code. In some embodiments, the notification module 510 transmits a patient flag notification based on flagging the patient as not have the anticipated diagnosis code and receives a patient flag response in response to transmission of the patient flag notification. As per above, the patient flag notification may be received by the health plan device 102, the prescriber device 110, or otherwise. The receiver of the patient flag notification may make interventions or otherwise take actions to close a potential gap. The patient flag response may then identify the actions taken by the receiver In some embodiments, the code identification module 506 may use a predictive model (e.g., for matches not identified by clinical rules). In some embodiments, the predictive model or other predictive solution may be created from medical data combined with drug markers and demographic information. In some embodiments, the predictive model may be created from integrated medical and claims data that takes a template of drug markers and demographic information to predict who is likely to have a missing diagnosis code and/or patients likely to not have the anticipated diagnosis code.

The score calculation module 504 calculates a revised patient-score associated with the patient based on identification of the missing diagnosis code and/or identification of the patient as not having an anticipated diagnosis code. In general, the score revision is due to an intervention that was made as a result of the identification.

In general, an intervention is performed by or in accordance with the intervention module 508. In some embodiments, the intervention module 508 identifies patient and/or physician gaps. In some embodiments, the risk adjustment performed by the risk assessment and adjustment subsystem 202 includes, after intervention by the intervention module 508, recalculation of the adjusted risk score by the score calculation module 504 for each patient and for the health plan average after gap closure.

In some embodiments, the intervention module 508 facilitates an intervention to close a gap based identification of the missing diagnosis code and/or identification of the patient as not having an anticipated diagnosis code. The intervention may be performed manually (e.g., by nurses), electronically (e.g., by e-mailing a prescriber through the prescriber device 110), or otherwise. Interventions in the form of text messages, e-mail with interactive web conversation, 340b type hospital strategy, or the like may be made. Other types of interventions may also be used. In some embodiments, the intervention module 508 directs claims re-submission and/or a diagnosis adjustment.

In some embodiments, the intervention module 508 includes involvement with health risk assessments (HRAs). HRAs may be performed upfront to prevent missing diagnosis codes or the patient not having the anticipated diagnosis code. In some embodiments, a kiosk or portal may be used to connect with health plans on the exchange (e.g., through the health plan device 102 and/or the exchange device 108). In some embodiments, activating a health benefit may include a mandatory health risk assessment as a starting point. In some embodiments, the benefit manager may partner with navigators, who are reimbursed for new enrollees that complete a health risk assessment.

In some embodiments, the intervention module 508 includes involvement with physician office programs for claims re-submission. Clinicians in the field or available through other communication channels (e.g., phone outreach) may be used in conjunction with the intervention module 508 to target physicians or prescribers with highest concentration of missing diagnosis codes. Reports by the reporting module 516 may be run intermittently (e.g., monthly, quarterly, or the like) for a target physician list. Missing diagnosis messages may be integrated into doctor offices' current workflow through the prescriber device 102 or otherwise. A top-down approach may be used in conjunction with the intervention module 508 to target physician practices leadership and require diagnosis codes. Claim documents may be generated and/or sent to physician offices for their office in conjunction with the intervention module 508. Pre-populated claim documents may be created by or in conjunction with the intervention module 508 with suggested diagnosis codes that the physician's office could choose which one was accurate. The physician's office may either submit a claim for billing (e.g., through the prescriber device 110 or otherwise) or the benefit manager could perform this function (e.g., by the benefit manager device 106) on behalf of the physician's office.

In some embodiments, the intervention module 508 includes involvement with telemedicine. A team may fill in missing diagnosis codes or partners with doctors' offices to do so in conjunction with the intervention module 508.

In some embodiments, the intervention module 508 records intervention information (e.g., in the database 112) regarding an intervention to close a gap based on identification of the missing diagnosis code and/or identification of the patient as not having an anticipated diagnosis code. Calculation of the revised patient-score associated with the patient by the score calculation module 504 may then based on recordation of the intervention information.

In some embodiments, the code identification module 506 transmits a missing diagnosis code request regarding the missing diagnosis code based on identification of the missing diagnosis code and receives a missing diagnosis code response in response to transmission of the missing diagnosis code request. In general, the missing diagnosis code response reflects inclusion of the missing diagnosis code in an electronic medical record of the patient. The recordation of the intervention information by the intervention module 508 may then be based on receipt of the missing diagnosis code response. The inclusion of the missing diagnosis code in the electronic medical record may include modification to an existing medical claim in the medical claims history, addition of a new medical claim in the medical claims history, or the like.

The missing diagnosis may be captured in conjunction with the intervention module 508 through medication therapy management (MTM), televisits, diagnosis code collection, or the like.

In some embodiments, clients may be asked to provide the diagnosis codes to the intervention module 508 as they are captured on medical claims from physician offices or hospital admissions (e.g., through the prescriber device 110).

In some embodiments, if there is any prior authorization criterion being reviewed, the intervention module 508 may request the diagnosis as part of the criteria required for the review and then obtain the diagnosis code via that process. In an example embodiment, the request of the diagnosis by the intervention module 508 may function in embodiments whether the drug was a prior authorization required drug. For example, the request may be made by or in conjunction with the intervention module 508 through the physician using an online prior authorization (e.g., through the prescriber device 110) to enter the diagnosis and medical information.

In some embodiments, the list of patients that have a diagnosis capture opportunity may be provided by the intervention module 508 to respective clients and/or health plans. The clients and/or health plans may use case workers and physician audit teams to capture the actual diagnosis.

In some embodiments, a list of patients that are believed to be missing a diagnosis code are provided to the health plan device 102 along with associated evidence for the basis for inclusion by the intervention module 508. Health plan clients may then decide on the best way to approach either the patient or the physician in order to have the appropriate diagnosis code entered into the patient's record.

In some embodiments, the pharmacist filling the drug may be directed to enter the diagnosis code when known in conjunction with the intervention module 508. The direction by or in conjunction with the intervention module 508 may be made electronically (e.g., via e-mail), via letter, via person-to-person communication, or otherwise. In some embodiments, the intervention module 508 may direct the physician offices to fill in the diagnosis codes.

In some embodiments, the patient's physician may be approached in conjunction with the intervention module 508 in a similar manner as to how the patient's physician is approached regarding drug rules. The patient's physician may be presented with the basis for why the patient needs the ICD-9 code and/or ICD-10 code and if the patient's physician will confirm the analysis and/or ask the patient's physician to be sure to enter the diagnosis code on the patient's next visit.

In some embodiments, the physician is e-enabled and a clinical interoperability message or a MEDCO CHANGERX transaction may be leveraged by or in conjunction with the intervention module 508 to request a diagnosis code for the specific prescription. The physician may then be educated on submitting that diagnosis code on the medical claim for the patient.

In some embodiments, the physician's office may be contacted by or in conjunction with the invention module 508 with a list of patients predicted to have a missing code and the physician's office may be asked to resolve it. In some embodiments, the benefit manager may resolve it. In some embodiments, the physician's office may benefit from adding the codes by receiving administrative fees.

In some embodiments, a predictive model may be created by the intervention module 508 for who will close the gaps themselves. Other people may be targeted with an intervention by the intervention module 508 to obtain missing codes filled.

In some embodiments, the score calculation module 504 calculates a plan-level average risk score associated with a benefit plan (e.g., including the patient as a member of the benefit plan and calculates a revised plan-level average risk score associated with a benefit plan based on identification of the missing diagnosis code and/or identification of the patient as not having an anticipated diagnosis code. The notification module 510 may then transmit a score notification regarding the revised patient-level risk score, the revised plan-level average risk score, or both the revised patient-level risk score and the revised plan-level average risk score. Reimbursement or notification of reimbursement may be received by the accounting module 512 based on transmission of the score notification.

In some embodiments, the notification module 510 transmits the score notification to a client device (or the health plan device 102) and reimbursement (or notice of reimbursement) is received by the accounting module 512 from a client associated with the client device (or the health plan associated with the health plan device 102).

In some embodiments, the notification module 510 transmits the score notification to a governmental device (or the exchange device 108) and the reimbursement (or notice of reimbursement) is received by the accounting module 512 in the form of an adjustment from a governmental organization associated with the governmental device (or an exchange).

In some embodiments, the revised plan-level average risk score is compared against a state average risk score by the analysis module 514. An amount of reimbursement received by the accounting module 512 (or indicated in the notice received by the accounting module 512) is based on comparison of the revised plan-level average risk score against the state average risk score by the analysis module 514.

The analysis module 514 documents conditions that support drug code-to-condition mapping and analyzes a patient population associated with the benefit plan to identify the patient as having a condition among the conditions that support drug code-to-condition mapping.

In some embodiments, the score calculation module 504 calculates a plan-level average risk score associated with a benefit plan and calculates a revised plan-level average risk score associated with a benefit plan based on identification of the missing diagnosis code and/or identification of the patient as not having an anticipated diagnosis code. The analysis module 514 compares the revised plan-level average risk score against a state average risk score. The notification module 510 then transmits an adjustment notification (e.g., to the exchange device 108) based on a result of a comparison of the revised plan-level average risk score against a state average risk score by the analysis module 514.

The reporting module 516 may be used to generate a report for one, or more than one, of the entities or devices associated with the system 100. For example, the reporting module 512 may generate a patient-level details report that includes, for a plan population associated with the benefit plan, the patient-level risk score, a number of gaps, a condition associated with a particular gap, or combinations thereof.

Figure 6:
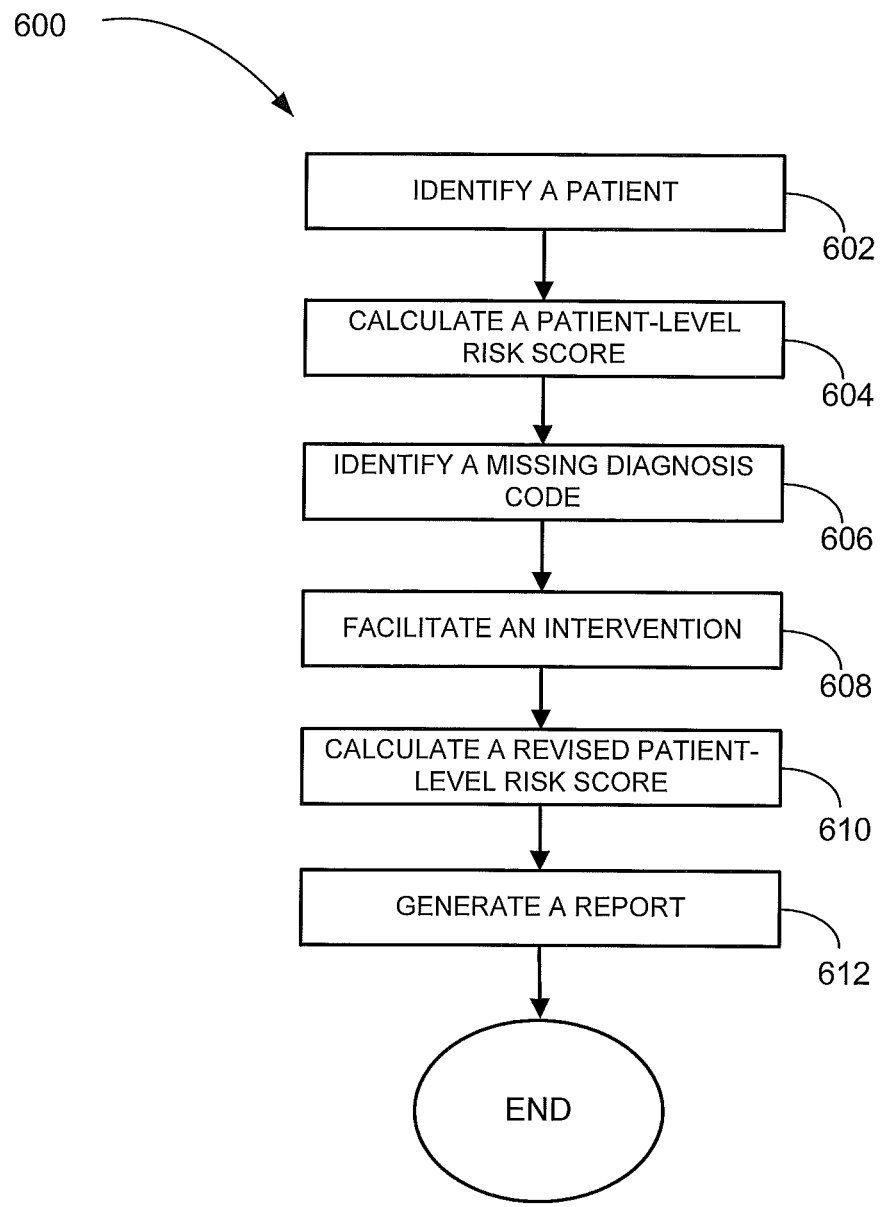
FIGS. 6-9 are example process flows illustrating methods for performing risk assessment and adjustment, according to an example embodiment.

FIG. 6 illustrates a method 600 for performing risk assessment and adjustment, according to an example embodiment. The method 600 may be performed by the health plan device 102, the benefit manager device 106, the exchange device 108, partially by two or more than two of the devices 102, 106, and 108, or may be otherwise performed.

A patient, or a number of patients, may be identified at block 602 for analysis. In some embodiments, a number of conditions that support drug code-to-condition mapping may be document and a patient population associated with the benefit plan may be analyzed to identify the patient as having a condition among the conditions that support drug code-to-condition mapping. In some embodiments, advanced analytics may be used to identify patients that probably have a diagnosis but do not have a diagnosis code.

A patient-level risk score associated with a patient is calculated at block 604. A single risk score for a single patient may be calculated, or a risk score may be calculated for each of a number of patients of a patient population. These patients may be identified based on the aforementioned described operations.

In some embodiments, calculation of the patient-level risk score includes accessing medical claims associated with the patient, calculating a demographic risk score, calculating a patient diagnostic risk score, and combining (e.g., by summing) the demographic risk score and the patient diagnostic risk score to calculate the patient-level risk score. The accessing of medical claims may be based on a professional source of diagnosis, an inpatient facility source of diagnosis, and/or an outpatient facility source of diagnosis.

In some embodiments, calculation of the demographic risk score includes assigning a demographic value to the patient based on age and gender of the patient and calculating the demographic risk score based on assignment of the demographic value. In some embodiments, calculation of the patient-level risk score at multiple plan tiers.

A missing diagnosis code associated with the patient is identified based on medical claims history of the patient, historical prescription drug claims of the patient, and a drug marker is identified at block 606. By identifying the missing diagnosis code, a diagnosis may be associated with the patient that was not previously identified in the electronic medical record of the patient.

In some embodiments, identification of the missing diagnosis code includes comparing the medical claims history of the patient to the historical prescription drug claims of the patient for the drug marker, determining that the patient does not have a medical claim associated with the drug marker based on comparison of the medical claims history to the historical prescription drug claims, and flagging the patient as having the missing diagnosis code.

In some embodiments, a determination that the patient does not have a medical claim associated with the drug marker is based on comparison of the medical claims history to the historical prescription drug claims and a drug code-to-condition mapping.

In some embodiments, a patient flag notification is transmitted based on flagging the patient as having the missing diagnosis code and a patient flag response is received in response to transmission of the patient flag notification.

In some embodiments, identification of the missing diagnosis code includes comparing the medical claims history of the patient to the historical prescription drug claims of the patient for the drug marker, determining that the patient does not have a medical claim associated with the drug marker based on comparison of the medical claims history to the historical prescription drug claims, and associating the missing diagnosis code with the patient.

In some embodiments, a determination may be made at block 606 (and/or block 602) that the missing condition or diagnosis code was not a result of "rule out" logic that is used to eliminate false positives. For example, medical conditions sent by a client to a benefit manager may not be loaded by the benefit manager unless the medical conditions met certain criteria. For example, a condition could include that there are two, three, or more separate claims on different dates of services with the diagnosis indicated, that the claims had to be from a service or procedure and not a lab test or a diagnostic test, or the like. In another example, if the source of the information is from a claim, the condition may not be displayed on a member's profile if was straight from a health assessment questionnaire or from a pharmacist discussion with the member.

An intervention may be facilitated at block 608 to close a gap based identification of the missing diagnosis code. In some embodiments, intervention information is recorded regarding an intervention to close a gap based on identification of the missing diagnosis code.

In some embodiments, a missing diagnosis code request is transmitted regarding the missing diagnosis code based on identification of the missing diagnosis code and a missing diagnosis code response may be received in response to transmission of the missing diagnosis code request. The missing diagnosis code response may reflect inclusion of the missing diagnosis code in an electronic medical record of the patient.

A revised patient-level risk score associated with the patient is calculated at block 610 based on identification of the missing diagnosis code. In some embodiments, calculation of the revised patient-score associated with the patient is based on the intervention, recordation of the intervention information, or the like.

In some embodiments, a plan-level average risk score associated with a benefit plan is calculated and a revised plan-level average risk score associated with a benefit plan is calculated based on identification of the missing diagnosis code.

A score notification regarding the revised patient-level risk score, the revised plan-level average risk score, or both the revised patient-level risk score and the revised plan-level average risk score may then be transmitted. In some embodiments, the score notification is transmitted to a client device and the reimbursement is received from a client associated with the client device. In some embodiments, the score notification is transmitted to a governmental device and the reimbursement is received in the form of an adjustment from a governmental organization associated with the governmental device.

Reimbursement may then be received based on transmission of the score notification. In some embodiments, the revised plan-level average risk score is compared against a state average risk score. An amount of the reimbursement may then be based on comparison of the revised plan-level average risk score against the state average risk score.

In some embodiments, a plan-level average risk score associated with a benefit plan is calculated and a revised plan-level average risk score associated with a benefit plan based on identification of the missing diagnosis code is calculated. The revised plan-level average risk score may then be compared against a state average risk score. An adjustment notification may be transmitted based on a result of a comparison of the revised plan-level average risk score against a state average risk score.

A report may be generated at block 612. For example, a patient-level details report may be generated that includes for a plan population associated with the benefit plan, the patient-level risk score, a number of gaps, a condition associated with a particular gap, or the like. Other types of reports may also be generated.

Figure 7:
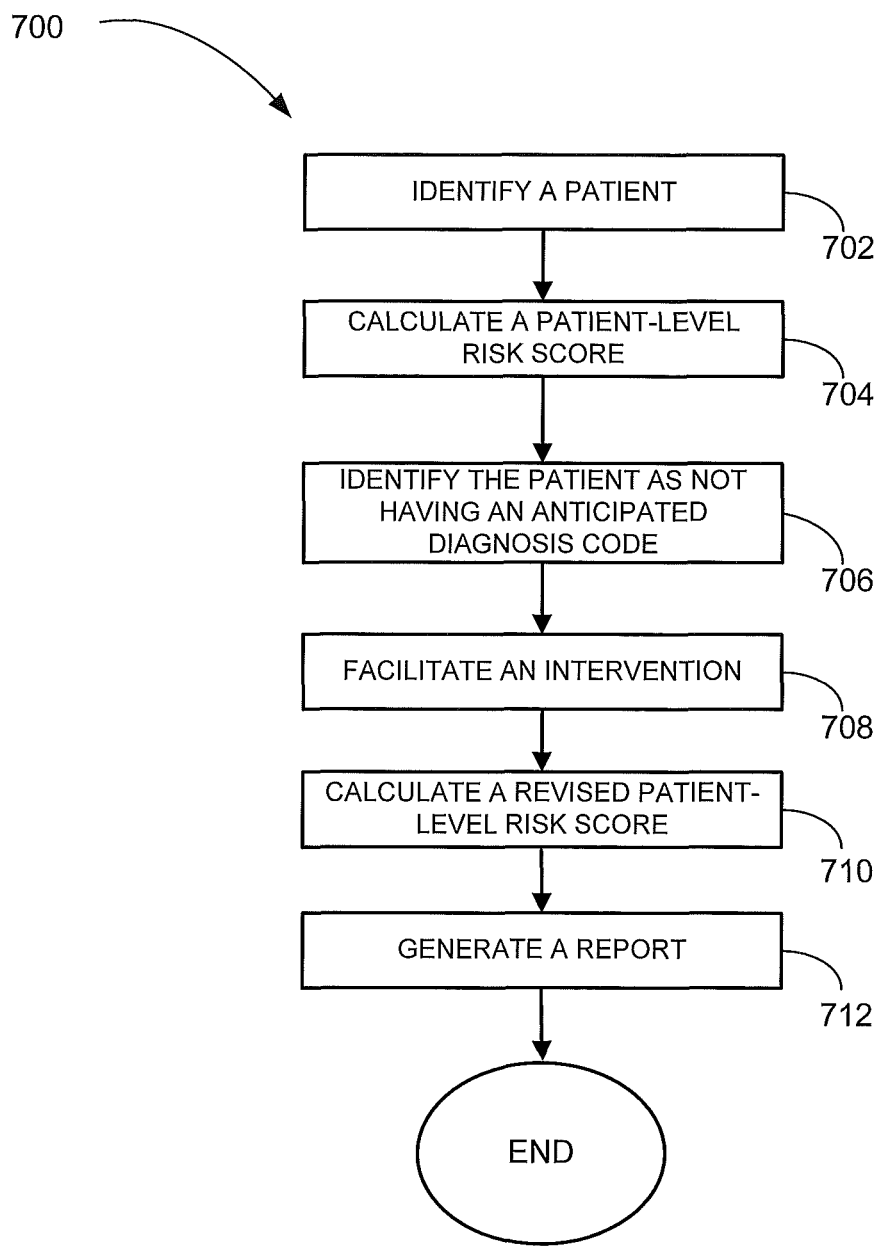

FIG. 7 illustrates a method 700 for performing risk assessment and adjustment, according to an example embodiment. The method 700 may be performed by the health plan device 102, the benefit manager device 106, the exchange device 108, partially by two or more than two of the devices 102, 106, and 108, or may be otherwise performed.

A patient, or a number of patients, may be identified at block 702 for analysis. In some embodiments, a number of conditions that support drug code-to-condition mapping may be document and a patient population associated with the benefit plan may be analyzed to identify the patient as having a condition among the conditions that support drug code-to-condition mapping.

A patient-level risk score associated with a patient is calculated at block 704. A single risk score for a single patient may be calculated, or a risk score may be calculated for each of a number of patients of a patient population. These patients may be identified based on the aforementioned described operations.

The patient is identified as not having an anticipated diagnosis code based on medical claims history of the patient, historical prescription drug claims of the patient, and a drug marker at block 706.

In some embodiments, identification includes comparing the medical claims history of the patient to the historical prescription drug claims of the patient for the drug marker, determining that the patient has the drug marker but does not have the anticipated diagnosis code of a medical claim associated with the drug marker, and flagging the patient as not having the anticipated diagnosis code and/or associating the anticipated diagnosis code with the patient.

In some embodiments, a determination that the patient does not have an anticipated diagnosis code is based on comparison of the medical claims history to the historical prescription drug claims and a drug code-to-condition mapping.

In some embodiments, a patient flag notification is transmitted based on flagging the patient as not having the anticipated diagnosis code and a patient flag response is received in response to transmission of the patient flag notification.

An intervention may be facilitated at block 708 to close a gap based identification of not having the anticipated diagnosis code.

In some embodiments, an unanticipated diagnosis code request is transmitted regarding the unanticipated diagnosis code based on identification of the unanticipated diagnosis code and an unanticipated diagnosis code response may be received in response to transmission of the unanticipated diagnosis code request. The unanticipated diagnosis code response may reflect correction of a diagnosis code in an electronic medical record of the patient.

A revised patient-level risk score associated with the patient is calculated at block 710 based on identification of the unanticipated diagnosis code. In some embodiments, calculation of the revised patient-score associated with the patient is based on the intervention, recordation of the intervention information, or the like.

A report may be generated at block 712. For example, a patient-level details report may be generated that includes for a plan population associated with the benefit plan, the patient-level risk score, a number of gaps, a condition associated with a particular gap, or the like. Other types of reports may also be generated.

Figure 8:
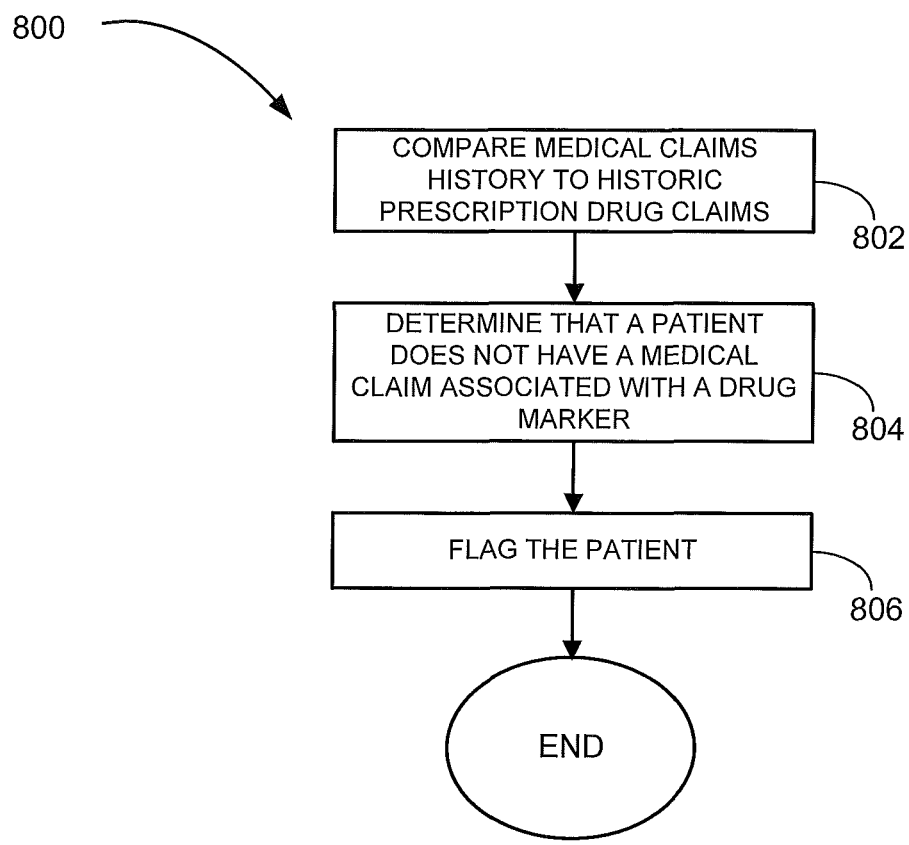

FIG. 8 illustrates a method 800 for performing risk assessment and adjustment, according to an example embodiment. The method 800 may be performed by the health plan device 102, the benefit manager device 106, the exchange device 108, partially by two or more than two of the devices 102, 106, and 108, or may be otherwise performed.

A comparison of the medical claims history of a patient to historical prescription drug claims of the patient for a drug marker is made at block 802.

A determination that the patient does not have a medical claim associated with the drug marker based on comparison of the medical claims history to the historical prescription drug claims is made at block 804.

At block 806, the patient is flagged as having a missing diagnosis code, the patient as not having an anticipated diagnosis, or both having a missing diagnosis code and as not having an anticipated diagnosis.

Figure 9:
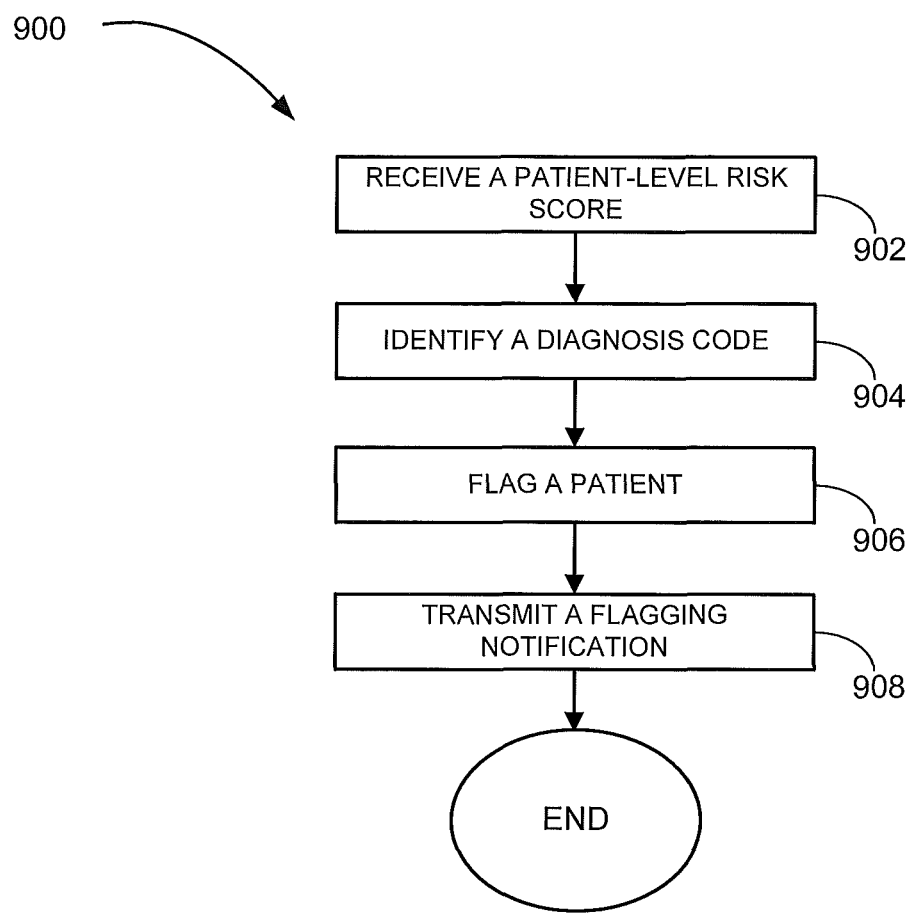

FIG. 9 illustrates a method 900 for performing risk assessment and adjustment, according to an example embodiment. The method 900 may be performed by the health plan device 102, the benefit manager device 106, the exchange device 108, partially by two or more than two of the devices 102, 106, and 108, or may be otherwise performed.

A patient-level risk score associated with a patient is received at block 902. A missing diagnosis code and/or an unanticipated diagnosis code associated with the patient is identified at block 904 based on medical claims history of the patient, historical prescription drug claims of the patient, and a drug marker. At block 906, the patient is flagged based on identification of the missing diagnosis code and/or an unanticipated diagnosis code. A flagging notification is transmitted at block 908 based on flagging of the patient.

Various operations may be performed during the methods 600-900 may be performed interchangeably with other methods 600-900. For example, an operation performed during the method 600 may be performed during the method 900 with or without modification based on context of the method.

In some embodiments, the methods and systems may enable a party to become the engine to quickly identify patients at risk without diagnosis codes. A fee may then be charged to certain types of access to the database 112 (e.g., and become an engine behind EMR systems).

In some embodiments, electronic prior authorization (PA) while patient is in the physician's office may be affected by the methods and systems. For example, when conditions are highly reimbursed, a prior authorization to the prescriber (e.g., physician) to confirm ICD-9 to move control upfront may be made. In some embodiments, the methods and systems may be licensed to current or future clients (e.g., EMR vendors).

In some embodiments, the methods and systems may be used with EMR related data. An entity responsible for EMR may then offer the methods and systems into accountable care organizations (ACOS) and/or hospital systems.

In some embodiments, the benefit manager may partner with an EMR vendor to gain access to their health client base. The EMR vendor may then provide the benefit manager with data, and the benefit manager would use the methods and systems to provide a risk assessment output. The risk assessment output may include a list of patients with missing diagnosis codes or the like.

In some embodiments, a portal or partnership with the EMR vendor may be made to go into physician records to close gaps or flag patients with open gaps. Example patient types include patients that visited their physician but are missing a diagnosis code and patients that did not visit physician and are undiagnosed with disease state, but would have diagnosis code/added risk once they see their physician.

FIG. 10 is an example diagram, according to an example embodiment. The diagram 1000 reflected in FIG. 10 includes a chart for risk assessment and adjustment that reflects on how to identify conditions for a POC.

Figure 11:
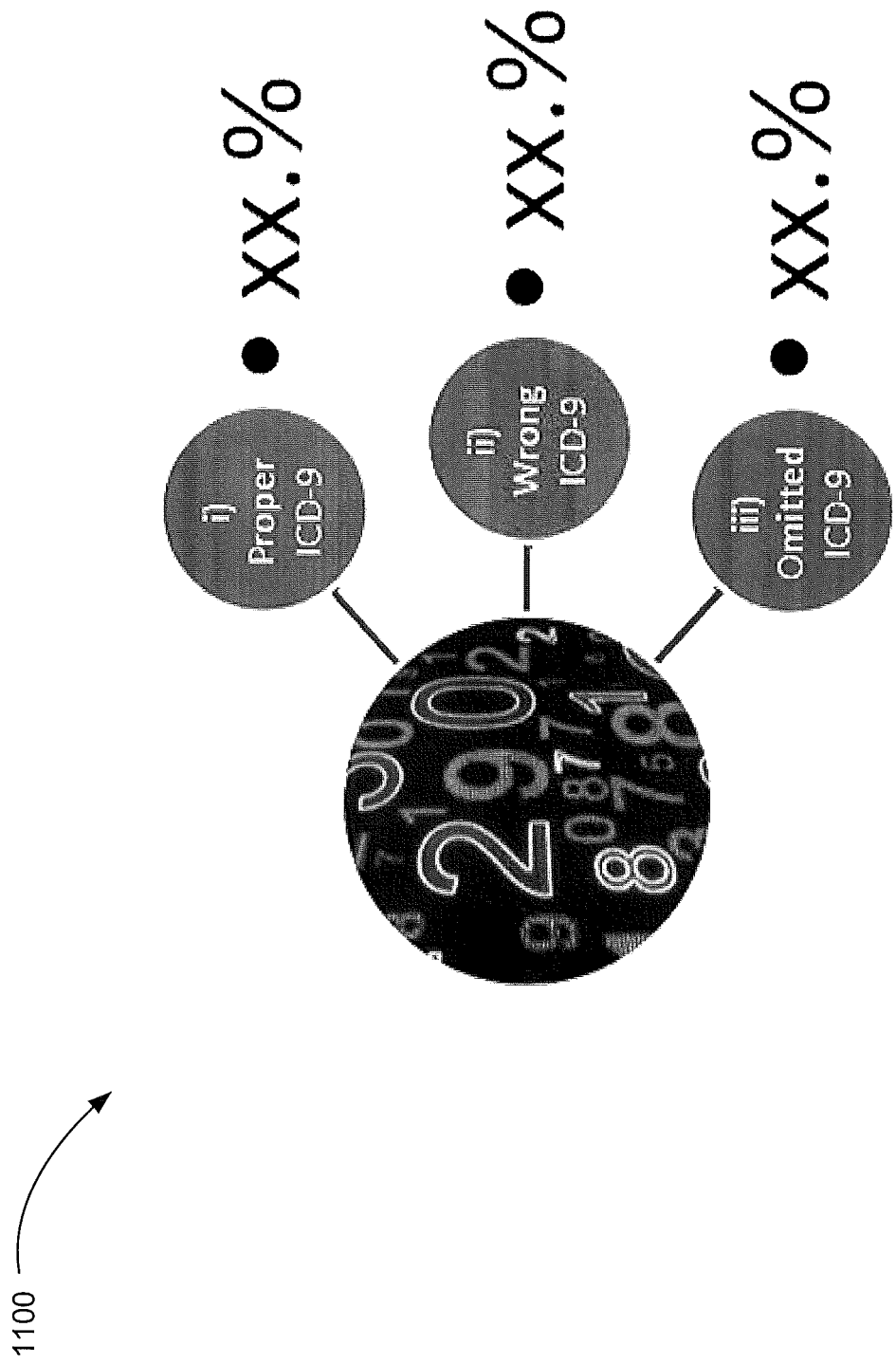

FIG. 11 is an example diagram, according to an example embodiment. The diagram 1100 reflected in FIG. 11 includes an example of a basis for creating an implementation of an ICD-9 diagnosis model.

By way of example, consideration may be made regarding patient population and ICD-9 accuracy. In general, ICD-9 codes for asthma/chronic obstructive pulmonary disorder (COPD) may originate in the medical claims data. An understanding of the "noise" within the diagnosis codes may be deemed relevant to model creation and/or usage. A question of how high the prevalence in wrong ICD-9 and omitted ICD-9 as reflected in the diagram 700 may be made. A determination may then be made as to whether these types of anomalies can be tolerated.

ICD-9 (an example of a medical diagnosis code) may be used as the initial reference point to whether a patient has the underlying condition. Clinical subject matter experts' inputs and rules may be used to validate.

ICD-9 codes may be assigned as follows:

| Definition Metric | Asthma/COPD | |
| --- | --- | --- |
| (1) ICD-9 Diagnosis Codes | 493.0 Extrinsic asthma | 491 Chronic bronchitis |
| | 493.1 Intrinsic asthma | 492 Emphysema |
| | 493.2 Chronic obstructive asthma | 493.2 Chronic obstructive asthma |
| | 493.8 Other fauns of asthma | 496 Chronic airway obstruction |
| | 493.9 Asthma, unspecified | |

Questions may then be made to clinical specialists as to whether asthma and COPD should be created and/or used as separate models or as a single algorithm. Questions may be made to clinical specialists as to what significant factors are traceable in the data and Rx history when analyzing Asthma I, II, III, IV.

A patient study selection may be made. The elements data may be sampled into a number of continuously eligible patients (e.g., 100,000, 200,000, 300,000, 400,000, 500,000 or more or less patients) with and without the underlying condition who are to be selected randomly from both the pharmacy data and the medical data.

Example conditions for the patient study selection may include that all patients are to be continuously eligible for at least 2 years at the time of sampling, all patients must be younger than a certain age (e.g., 65 years of age), and/or a patient's index date is to be determined based on his or her last filled prescription drug. Other conditions may also be used.

Test/validation data of patient attributes may be made after the patient sample is determined. For example, a benefit manager standard view of attributes for each patient may be made. ICD-9 diagnosis codes may be appended to each patient and they may be decoded as 0-1 dummy values.

By way of example, consideration may be made regarding patient population and ICD-9 accuracy. In general, ICD-9 codes for hemophilia may originate in the medical claims data. An understanding of the "noise" within the diagnosis codes may be deemed relevant to model creation and/or usage. A question of how high the prevalence in wrong ICD-9 and omitted ICD-9 as reflected in the diagram 700 may be made. A determination may then be made as to whether these types of anomalies can be tolerated.

ICD-9 may be used as the initial reference point to whether a patient has the underlying condition. Clinical subject matter experts' inputs and rules may be used to validate.

ICD-9 codes may be assigned as follows:
Hemophilia ICD-9 Codes
286.0 Congenital factor VIII disorder
286.1 Congenital factor IX disorder
286.2 Congenital factor XI deficiency
286.3 Congenital deficiency of other clotting factors Questions may then be made to clinical specialists as to whether separate male and female models should be made. A patient study selection may be made as described above. Test/validation data of patient attributes may be made after the patient sample is determined as described above.

Figure 12:
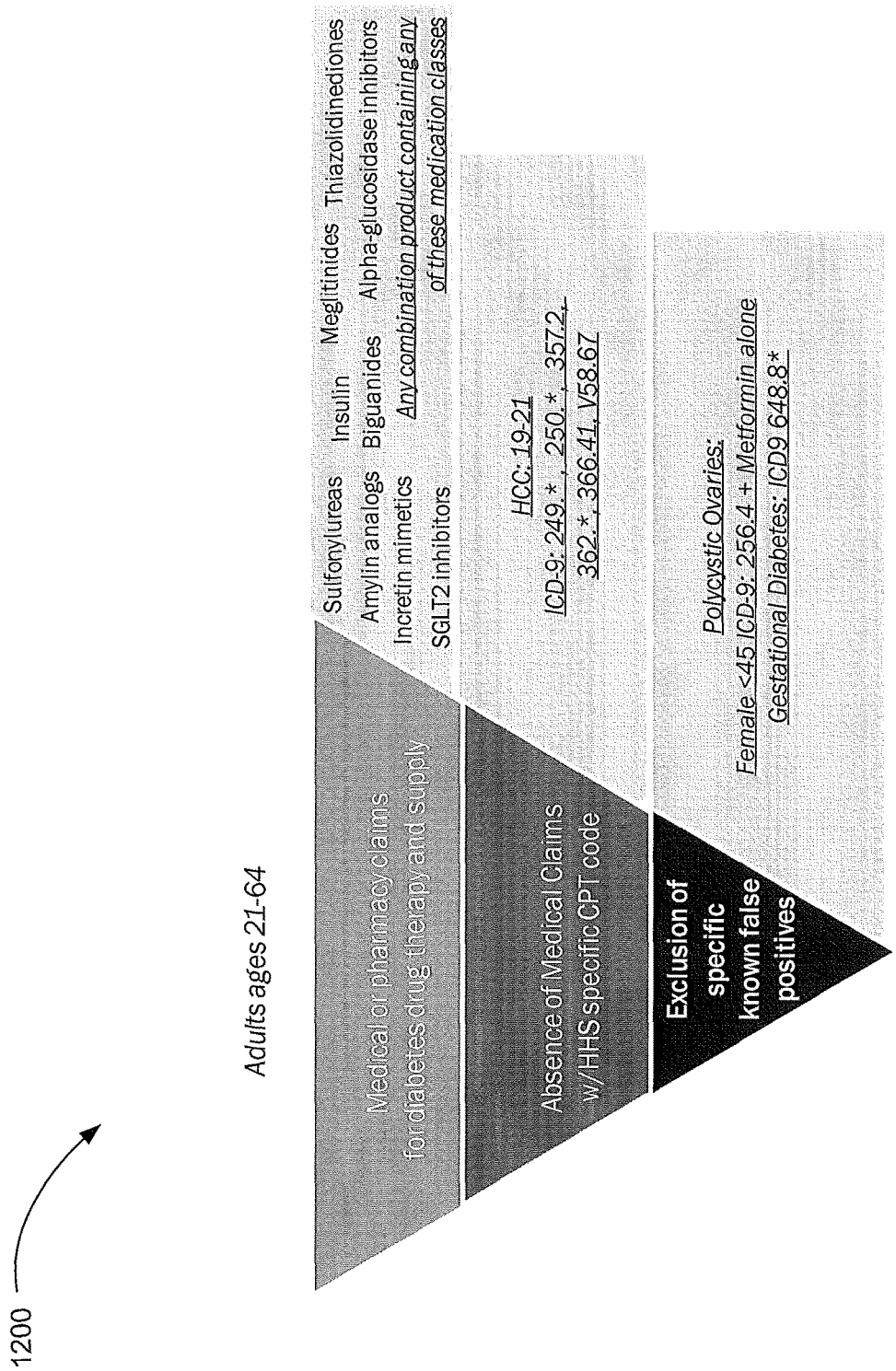

FIG. 12 is an example diagram, according to an example embodiment. The diagram 1200 reflected in FIG. 12 is an example, for diabetes where drugs and supplies have been identified in either pharmacy or medical claims that are drug markers for diabetes. The ICD9 code mapping may then be used to identify patients with a drug marker but no diagnosis code. Specific clinical exceptions may then be applied that lead to false positives. For example, for diabetes women under the age of 45 on metformin, a drug used for diabetes, may be using the prescription drug or supply for other conditions—such as polycystic ovary disease or gestational diabetes. Those specific patients may then be removed from targeted gaps.

Figure 13:
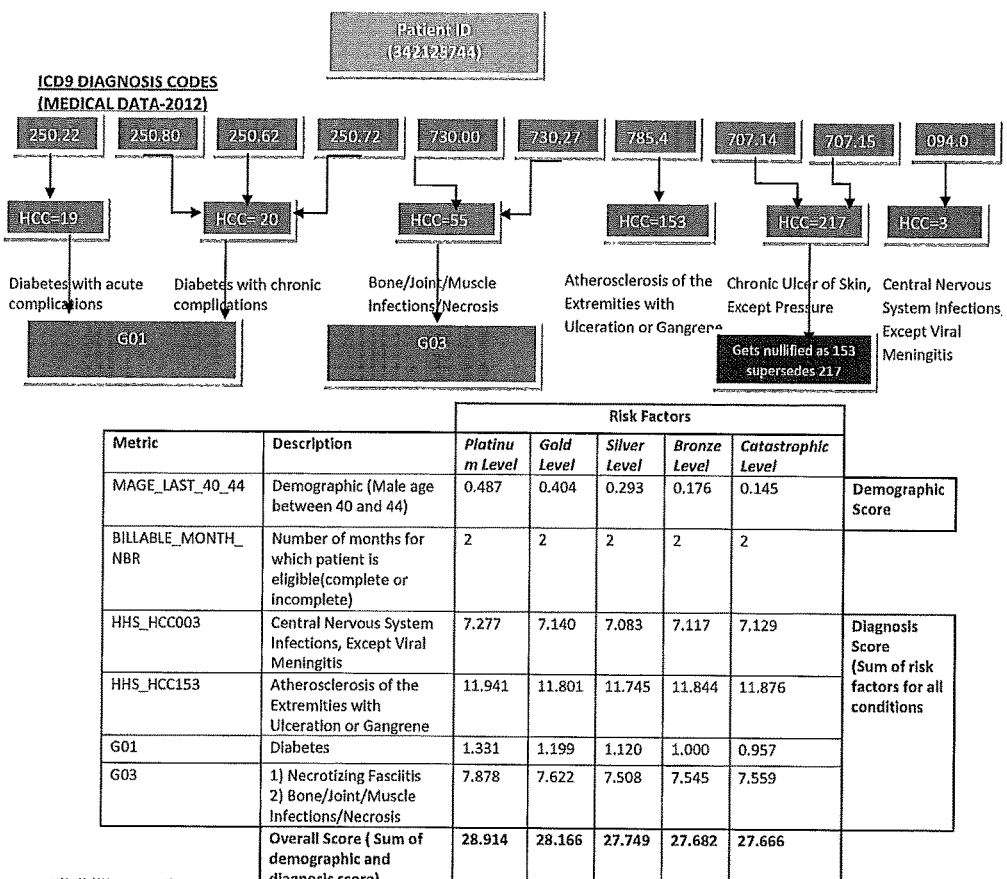

FIG. 13 is an example diagram, according to an example embodiment. The diagram 1300 reflected in FIG. 13 includes a patient having various diagnosis codes and their respective mappings into calculation of risk factors at various tier levels.

Figure 14:
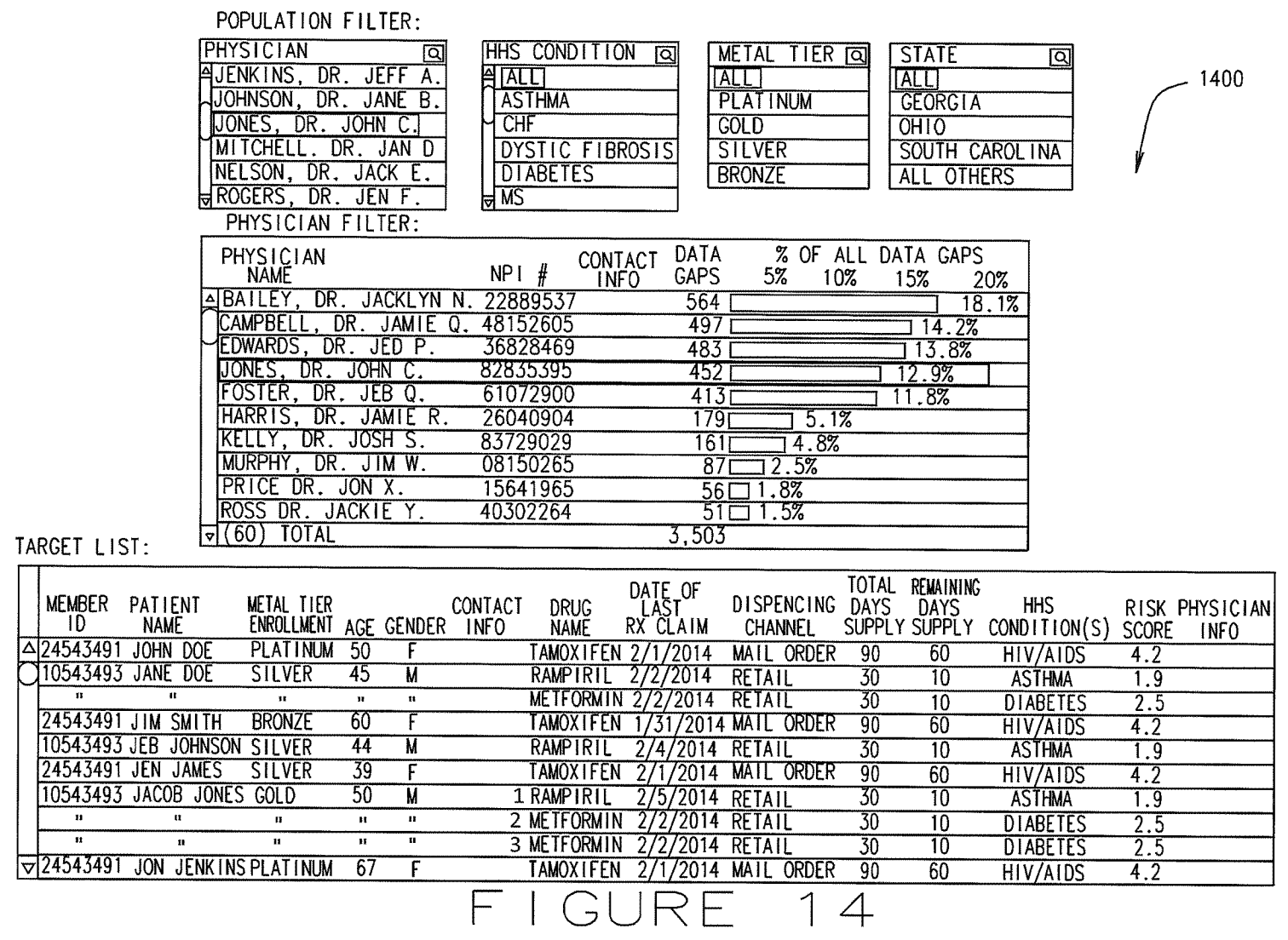

FIG. 14 is an example diagram, according to an example embodiment. The diagram 1400 reflected in FIG. 14 depicts fields needed to trigger the interventions for a particular offering.

Figure 15:
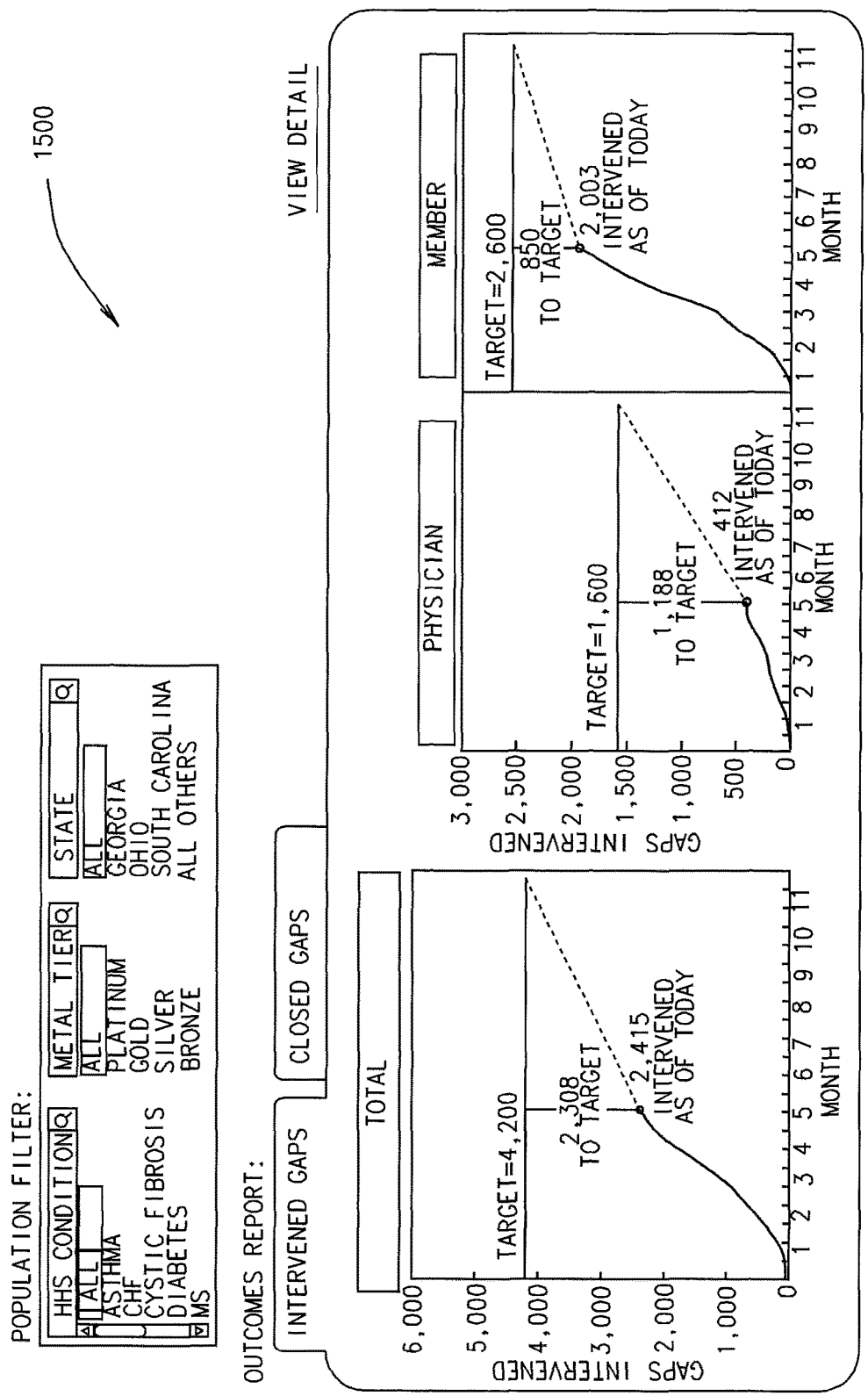

FIG. 15 is an example diagram, according to an example embodiment. The diagram 1500 reflected in FIG. 15 depicts the status of the interventions as being still open or closed as well as a summary of closed interventions.

FIG. 16 is an example diagram, according to an example embodiment. The diagram 1600 reflected in FIG. 16 depicts potential benchmarking capabilities by metal tier, condition, or at a consolidated state view.

Figure 17:
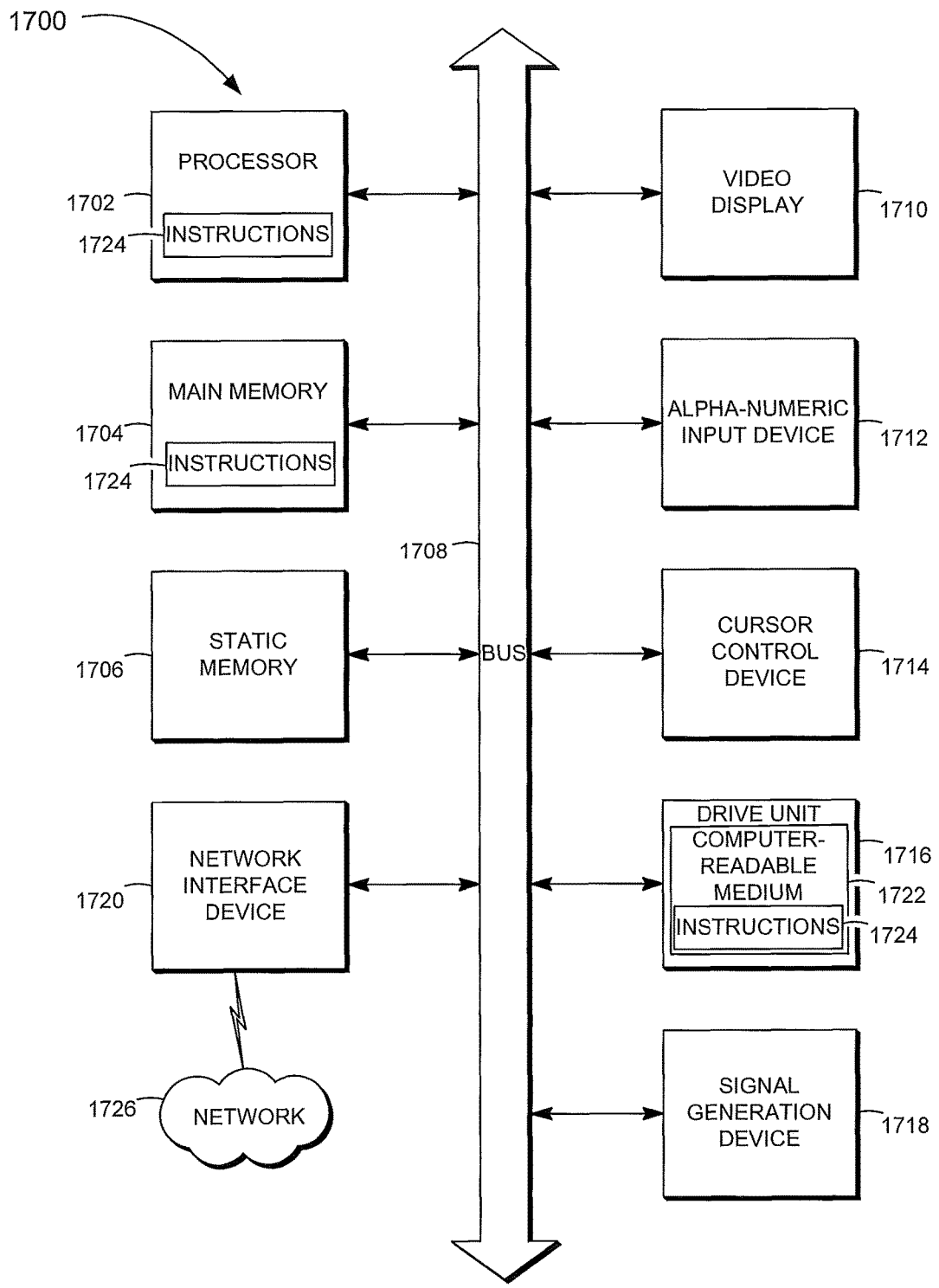
FIG. 17 is a block diagram of a machine in the example form of a computer system within which a set of instructions for causing the machine to perform any one or more of the methodologies discussed herein may be executed or stored.

FIG. 17 shows a block diagram of a machine in the example form of a computer system 1700 within which a set of instructions may be executed causing the machine to perform any one or more of the methods, processes, operations, or methodologies discussed herein. The health plan device 102, the benefit manager device 106, the exchange device 108, and/or the prescriber device 110 may include the functionality of the one or more computer systems 1700.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1700 includes a processor 1702 (e.g., a central processing unit (CPU) a graphics processing unit (GPU) or both), a main memory 1704 and a static memory 1706, which communicate with each other via a bus 1708. The computer system 1700 further includes a video display unit 1170 (e.g., a liquid crystal display (LCD) or a cathode ray tube (CRT)). The computer system 1700 also includes an alphanumeric input device 1712 (e.g., a keyboard), a cursor control device 1714 (e.g., a mouse), a drive unit 1716, a signal generation device 1718 (e.g., a speaker) and a network interface device 1720.

The drive unit 1716 includes a computer-readable medium 1722 on which is stored one or more sets of instructions (e.g., software 1724) embodying any one or more of the methodologies or functions described herein. The software 1724 may also reside, completely or at least partially, within the main memory 1704 and/or within the processor 1702 during execution thereof by the computer system 1700, the main memory 1704 and the processor 1702 also constituting computer-readable media.

The software 1724 may further be transmitted or received over a network 1726 via the network interface device 1720.

While the computer-readable medium 1722 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a patient-level risk score associated with a patient is calculated. A plan-level average risk score associated with a benefit plan is calculated. The patient is a member of the benefit plan. A missing diagnosis code associated with the patient is identified based on medical claims history of the patient, historical prescription drug claims of the patient, and a drug marker. A revised patient-score associated with the patient is calculated based on identification of the missing diagnosis code.

While the description generally reflects that certain methods, systems, and/or operations are performed by the benefit manager and associated device, the methods, systems, and/or operations may additionally or alternatively be performed by the health plan and associated device and/or the exchange and associated device.

Thus, methods and systems for risk assessment and adjustment have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A database management system comprising:
a prescriber device;
a database configured to store, for each user of a plurality of users, a set of codes indicating prior diagnoses for the user and a set of drug identifiers indicating prior drug prescriptions for the user; and
a review device comprising a memory and a processor that executes instructions from the memory, wherein the review device is remote from the prescriber device, and wherein the review device is configured to:
obtain a mapping between medical codes and corresponding drug markers;
select a subset of users from the plurality of users, wherein for each user of the subset of users, at least one of the set of drug identifiers in the database for the user is present in the mapping;
for each user of the subset of users, select a subset of the set of drug identifiers for the user by, for each drug identifier of the set of drug identifiers for the user in the database:
determining a corresponding medical code from the drug identifier according to the mapping,
searching the set of codes in the database for the user for the corresponding medical code
in response to identifying that the corresponding medical code is not present in the set of codes in the database for the user, including the drug identifier in the subset of drug identifiers; and
transmit the subset of drug identifiers for the subset of users to the prescriber device over a communications network,
wherein the prescriber device is configured to, in response to receiving drug identifiers, including a first drug identifier, from the review device:
generate a graphical display for an operator of the prescriber device, wherein the graphical display depicts (i) the first drug identifier and (ii) health information regarding a first user associated with the first drug identifier,
solicit a first diagnosis code corresponding to the first drug identifier, and
in response to receiving the first diagnosis code from the operator, transmit the first diagnosis code over the communications network to the review device, and
wherein the review device is configured to, in response to receiving the first diagnosis code from the prescriber device:
update the database to reflect the first diagnosis code in the set of codes corresponding to the first user,
calculate a first user-specific metric for the first user based on the updated database, and
selectively generate a display based on a plan-level metric, wherein the plan-level metric is based on a first weight and the first user-specific metric, and wherein the first weight is determined based on at least one of a demographic value, a Hierarchical Condition Category (HCC) value, and a severity value.

2. The system of claim 1 wherein the review device is configured to, in response to updating the database:
identify a plan-specific set of users of the plurality of users, wherein each user of the plan-specific set of users is associated with a first plan;
for each user of the plan-specific set of users other than the first user, calculate a user-specific metric; and
calculate the plan-level metric based on the user-specific metrics, including the first user-specific metric, of the plan-specific set of users.

3. The system of claim 2 wherein the review device is configured to transmit a request for reimbursement based on the plan-level metric.

4. The system of claim 3 wherein the review device is configured to transmit the request for reimbursement based on a difference between the plan-level metric and an average metric across a plurality of plans.

5. The system of claim 4 wherein the average metric is calculated across a population of a state in which the first plan is offered.

6. The system of claim 2 wherein the plan-level metric is calculated based on a weighted combination of the user-specific metrics of the plan-specific set of users, wherein the weight for each of the user-specific metrics in the weighted combination is determined based on at least one of a demographic value, a Hierarchical Condition Category (HCC) value, and a severity value.

7. The system of claim 1 wherein calculating the first user-specific metric for the first user includes:
  accessing, from the updated database, the set of codes for the first user and the set of drug identifiers for the first user;
  calculating a demographic metric;
  calculating a user diagnostic metric; and
  calculating the first user-specific metric based on the demographic metric and the user diagnostic metric.

8. The system of claim 7 wherein calculating the demographic metric includes:
  assigning a demographic value to the first user based on age and gender of the first user; and
  calculating the demographic metric based on the demographic value.

9. The system of claim 1 wherein the review device is configured to:
  document a plurality of conditions that support mapping between codes and corresponding drug markers; and
  analyze a user population associated with a plan to identify the first user as having a condition among the plurality of conditions that support mapping between codes and corresponding drug markers.

10. The system of claim 1 wherein the review device is configured to:
  generate a user-specific details report that includes, for a plan population associated with a plan, at least one of (i) the first user-specific metric, (ii) the subset of drug identifiers for the first user, and (iii) a condition associated with a particular drug identifier of the subset of drug identifiers.

11. The system of claim 1 wherein the set of codes are selected from revision nine or greater of the International Classification of Diseases.

12. The system of claim 1 wherein the operator of the prescriber device is a medical care professional legally permitted to write a prescription for a medication.

13. The system of claim 1 wherein the first drug identifier of the first user corresponds to a therapy for a condition that supports mapping between medical codes and corresponding drug markers.

14. The system of claim 1 wherein the first drug identifier is a drug marker for a prescription drug that is usable to identify the first user as having a first medical condition.

15. A method comprising:
  storing, in a database, for each user of a plurality of users, a set of codes indicating prior diagnoses for the user and a set of drug identifiers indicating prior drug prescriptions for the user;
  at a review device, obtaining a mapping between medical codes and corresponding drug markers;
  at the review device, selecting a subset of users from the plurality of users, wherein for each user of the subset of users, at least one of the set of drug identifiers in the database for the user is present in the mapping;
  at the review device, for each user of the subset of users, selecting a subset of the set of drug identifiers for the user by, for each drug identifier of the set of drug identifiers for the user in the database:
  determining a corresponding medical code from the drug identifier according to the mapping;
  searching the set of codes in the database for the user for the corresponding medical code; and
  in response to identifying that the corresponding medical code is not present in the set of codes in the database for the user, including the drug identifier in the subset of drug identifiers;
  at a prescriber device, for a first drug identifier of the subset of drug identifiers:
  generating a graphical display for an operator, wherein the graphical display depicts (i) the first drug identifier and (ii) health information regarding a first user associated with the first drug identifier; and
  soliciting a first diagnosis code corresponding to the first drug identifier from the operator; and
  in response to receiving the first diagnosis code from the operator prescriber device:
  at the review device, updating the database to reflect the first diagnosis code in the set of codes corresponding to the first user;
  at the review device, calculating a first user-specific metric for the first user based on the updated database; and
  at the review device, selectively generating a display based on the updated database a plan-level metric, wherein the plan-level metric is based on a first weight and the first user-specific metric, and wherein the first weight is determined based on at least one of a demographic value, a Hierarchical Condition Category (HCC) value, and a severity value.

16. A non-transitory computer-readable medium comprising instructions that, when executed by one or more processors, cause the one or more processors to perform operations including:
  storing, in a database, for each user of a plurality of users, a set of codes indicating prior diagnoses for the user and a set of drug identifiers indicating prior drug prescriptions for the user;
  at a review device, obtaining a mapping between medical codes and corresponding drug markers;
  at the review device, selecting a subset of users from the plurality of users, wherein for each user of the subset of users, at least one of the set of drug identifiers in the database for the user is present in the mapping;
  at the review device, for each user of the subset of users, selecting a subset of the set of drug identifiers for the user by, for each drug identifier of the set of drug identifiers for the user in the database:
  determining a corresponding medical code from the drug identifier according to the mapping;
  searching the set of codes in the database for the user for the corresponding medical code; and
  in response to identifying that the corresponding medical code is not present in the set of codes in the database for the user, including the drug identifier in the subset of drug identifiers;
  at a prescriber device, for a first drug identifier of the subset of drug identifiers:
  generating a graphical display for an operator, wherein the graphical display depicts (i) the first drug identifier and (ii) health information regarding a first user associated with the first drug identifier; and soliciting a first diagnosis code corresponding to the first drug identifier from the operator; and in response to receiving the first diagnosis code from the operator prescriber device:

at the review device, updating the database to reflect the first diagnosis code in the set of codes corresponding to the first user;

at the review device, calculating a first user-specific metric for the first user based on the updated database; and at the review device, selectively generating a display based on the updated database a plan-level metric, wherein the plan-level metric is based on a first weight and the first user-specific metric, and wherein the first weight is determined based on at least one of a demographic value, a Hierarchical Condition Category (HCC) value, and a severity value.

* * * * *